US009277982B2

(12) United States Patent
Zunker et al.

(10) Patent No.: US 9,277,982 B2
(45) Date of Patent: *Mar. 8, 2016

(54) DISPOSABLE URINE INCONTINENCE DEVICE

(71) Applicant: Kimberly-Clark Worldwide, Inc., Neenah, WI (US)

(72) Inventors: MaryAnn Zunker, Oshkosh, WI (US); Sarah Anne Lemke, Appleton, WI (US); Particia Ann Samolinski, Winneconne, WI (US); Sarah Anne Olson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 17 days.

This patent is subject to a terminal disclaimer.

(21) Appl. No.: 14/150,001

(22) Filed: Jan. 8, 2014

(65) Prior Publication Data
US 2014/0135572 A1 May 15, 2014

Related U.S. Application Data

(63) Continuation of application No. 12/651,129, filed on Dec. 31, 2009, now Pat. No. 8,652,026.

(51) Int. Cl.
*A61F 2/00* (2006.01)
(52) U.S. Cl.
CPC ............... *A61F 2/0009* (2013.01); *A61F 2/005* (2013.01); *A61F 2210/0061* (2013.01); *Y10T 29/49838* (2015.01)

(58) Field of Classification Search
CPC ....... A61F 2/0009; A61F 2/02; A61F 2/0013; A61F 2/005; A61F 2210/0061
USPC ........... 600/29–32; 29/433; 604/15, 367, 374, 604/378, 358.23
See application file for complete search history.

(56) References Cited

U.S. PATENT DOCUMENTS

| 5,795,346 | A | 8/1998 | Achter et al. |
|---|---|---|---|
| 6,090,038 | A | 7/2000 | Zunker et al. |
| 6,679,831 | B1 | 1/2004 | Zunker et al. |
| 8,652,026 | B2 * | 2/2014 | Zunker et al. .................. 600/29 |
| 2002/0156343 | A1 | 10/2002 | Zunker |
| 2004/0158122 | A1 | 8/2004 | Guerquin |
| 2008/0033231 | A1 | 2/2008 | Bartning et al. |
| 2010/0016780 | A1 | 1/2010 | Vandenbogart et al. |
| 2011/0152813 | A1 | 6/2011 | Ellingson |

\* cited by examiner

*Primary Examiner* — Christine H Matthews
(74) *Attorney, Agent, or Firm* — Kimberly-Clark Worldwide, Inc.

(57) ABSTRACT

A disposable urinary incontinence device comprises a liquid-stable resilient member, and a cover sheet that envelops the liquid-stable resilient member to form an elongated member having a tubular profile. The elongated member has a first end, a second end, a first fold region disposed between the first end and the second end, a second fold region disposed between the first end and the first fold region, a third fold region disposed between the second end and the first fold region, a first portion located between the first end and the second fold region, a second portion located between the second end and the third fold region, a third portion located between the first fold region and a second fold region, and a fourth portion located between the first fold region and the third fold region to form a W-shaped incontinence device.

20 Claims, 18 Drawing Sheets

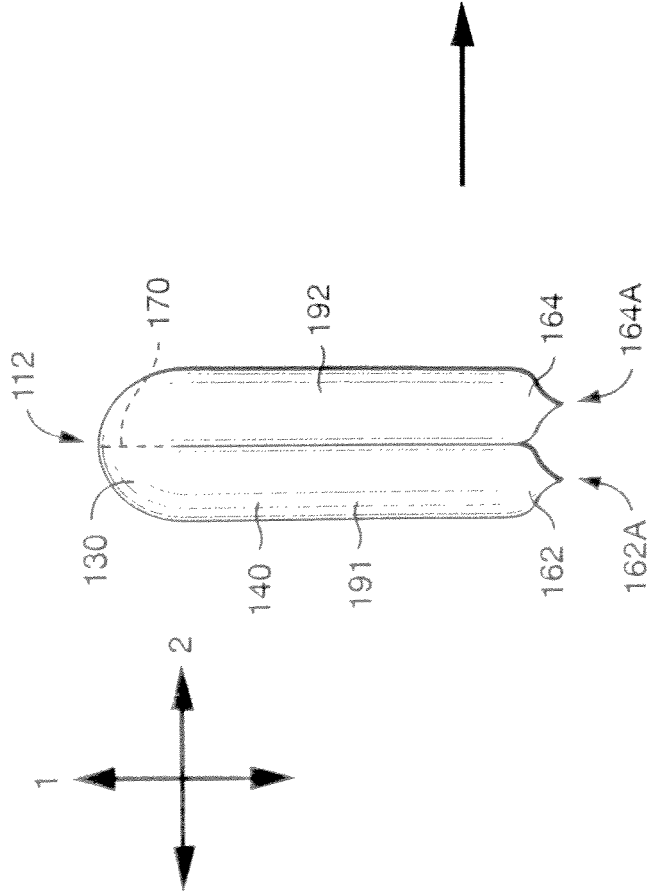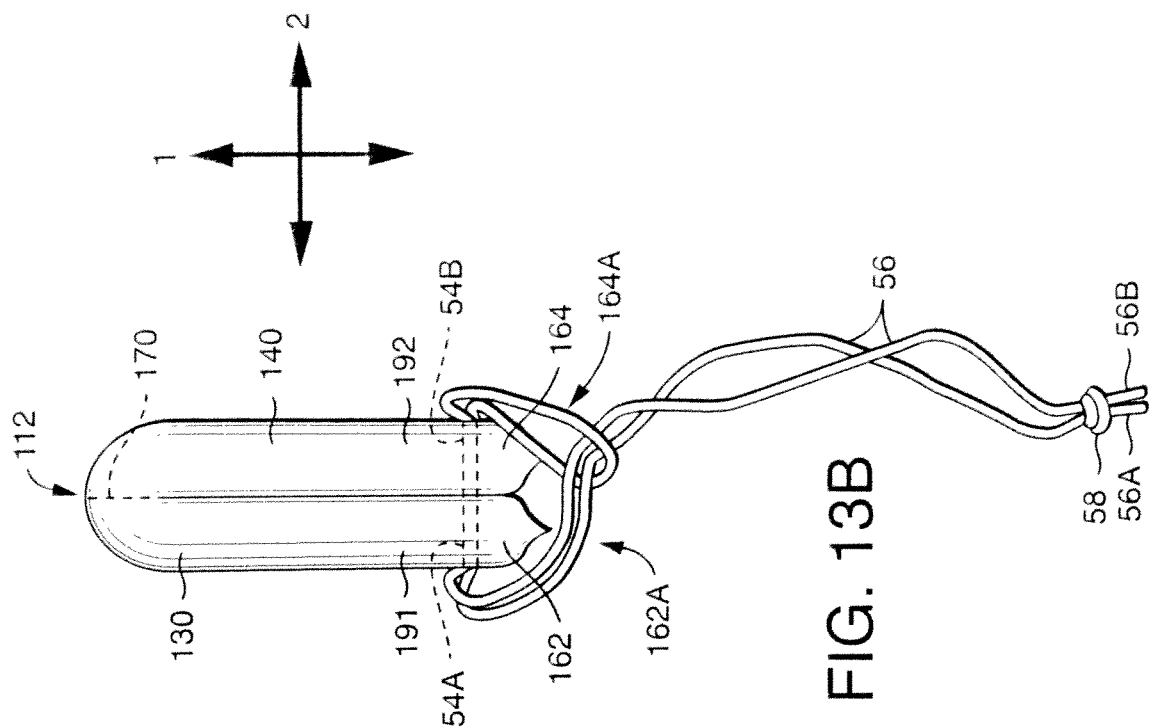

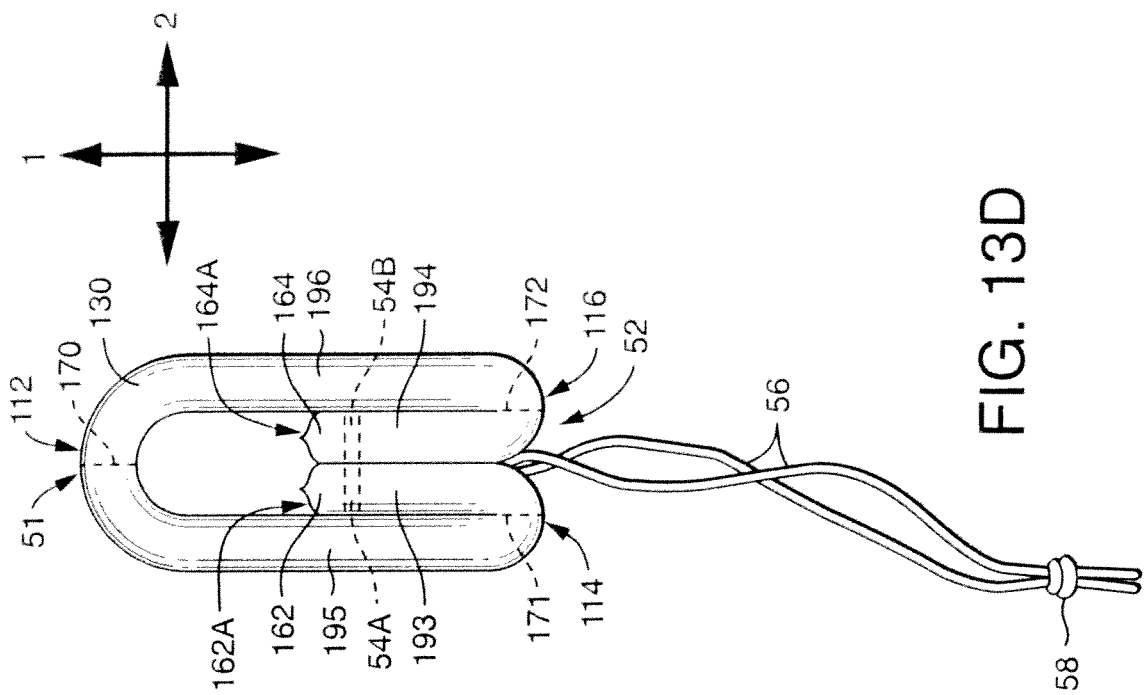
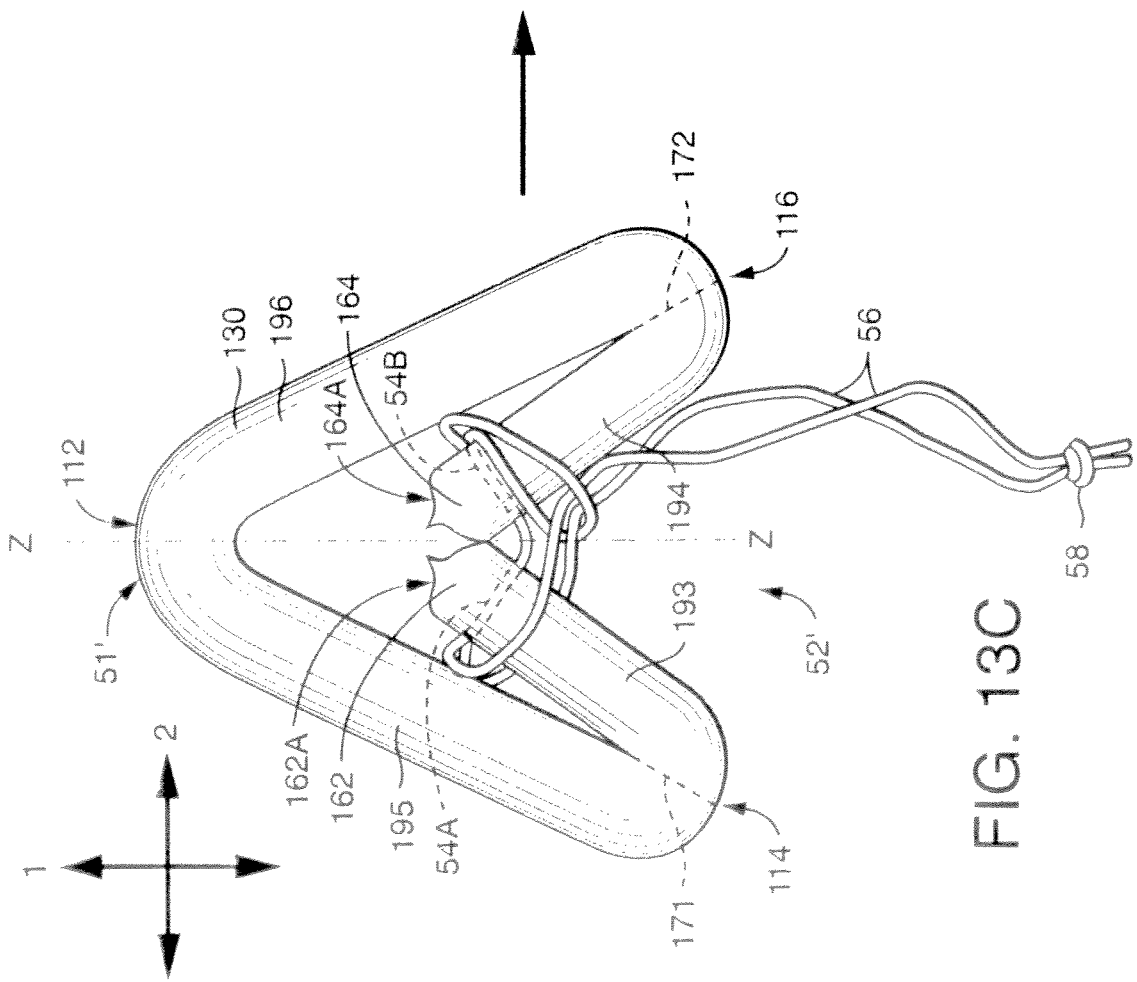

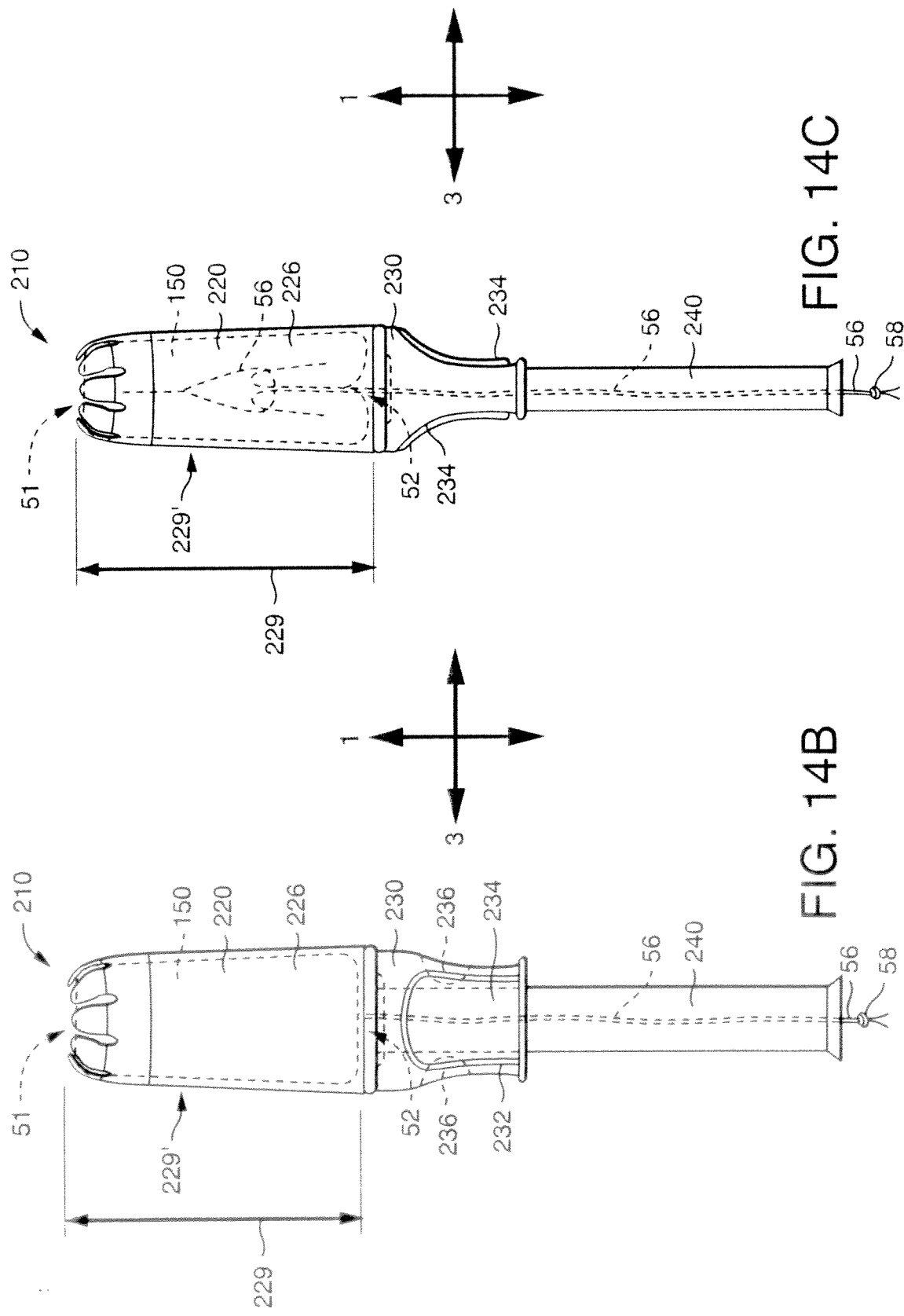

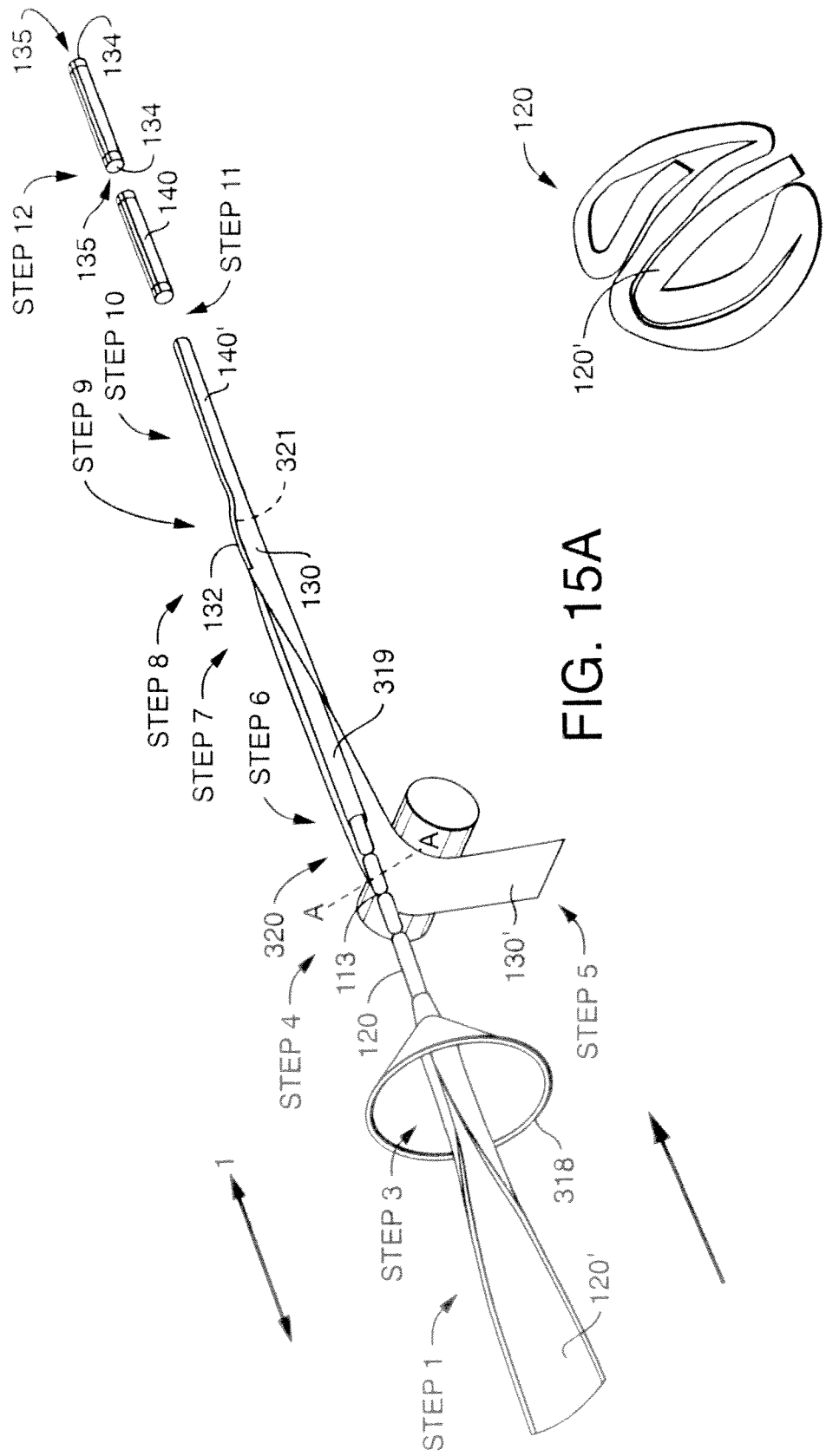

DISPOSABLE URINE INCONTINENCE DEVICE

BACKGROUND

Some women, especially women who have given birth to one or more children and/or older women, can experience incidences of involuntary urine loss due to stress urinary incontinence or combined stress and urge incontinence. For example, a sneeze or cough can increase the intra-abdominal pressure impinging on a person's bladder and cause the involuntary release of urine. The frequency and severity of such urine loss can increase as the muscles and tissues near the urethro-vaginal myofascial area grow weaker. It has also been recognized that the urinary sphincter muscle, which is located at the upper end of the urethra adjacent to the bladder, works well at sealing off the passing of urine from the bladder to the urethra when it has a round or circular cross-sectional configuration. However, when this passageway becomes distorted into a cross-sectional configuration having more of an elliptical or oval appearance, the sphincter muscle cannot close properly and the tendency for involuntary urine loss increases.

As the world's female population ages, though certainly not limited to women of age, there is an ever increasing need for a non-surgical procedure to reduce the involuntary urine loss commonly associated with "stress urinary incontinence." Today, there are a number of products available for this purpose. Essentially all of these products can only be purchased with a prescription and they typically require physical insertion and/or adjustment by a medical doctor or a nurse practitioner in order to perform correctly. In addition, most available urinary incontinence devices must be thoroughly cleansed and re-used, as opposed to being a one-time use disposable product.

Incontinent women who do not wish to use the current urinary incontinence devices attempt to prevent leakage onto garments by wearing absorbent pads or liners every day. However, this can be undesirable for many women. In addition, women who prefer to wear tampons for menstruation desire a non-pad product for managing their urine leakage needs and would find such a solution very attractive. Thus, there is a need for a disposable urinary incontinent device that extends beyond traditional solutions to provide for women's needs through all lifestages. In addition, the device would desirably be relatively low cost and could be purchased without a prescription. There is also a need for a urinary incontinence device which is less complicated than current devices and therefore more user friendly, and can be managed by the consumer without the intervention of a medical practitioner. Furthermore, there is a need for a urinary incontinence device which is easy for women to insert into and remove from their bodies, more comfortable to wear and provide psychological and realistic assurance that it is capable of properly performing over an extended period of time.

SUMMARY

In response to the needs discussed above, a disposable urinary incontinence device comprises a liquid-stable resilient member, and a cover sheet that envelops the liquid-stable resilient member to form an elongated member having a tubular profile. The elongated member has a first end, a second end, a first fold region disposed between the first end and the second end, a second fold region disposed between the first end and the first fold region, a third fold region disposed between the second end and the first fold region, a first portion located between the first end and the second fold region, a second portion located between the second end and the third fold region, a third portion located between the first fold region and a second fold region, and a fourth portion located between the first fold region and the third fold region. The elongated member is in a folded condition such that the first portion is substantially aligned adjacent to the second portion, the first portion is substantially aligned adjacent to the third portion, the second portion is substantially aligned adjacent to the fourth portion, and the first portion and the second portion are disposed between and adjacent to the third portion and the fourth portion to form a disposable urinary incontinence device having a W-shaped profile. In further aspects, the liquid-stable resilient member is non-absorbent, as measured by the Spinning Retention Capacity Test. In still further aspects, the liquid-stable resilient member has a resilient compression from 60% to 90% and a resilient expansion from 60% to 100%, as measured by the Resiliency Test. In yet further aspects, the liquid-stable resilient member is a surge material comprising a plurality of thermoplastic fibers heat bonded to one another to form a lofty nonwoven web having a basis weight of at least 20 grams per square meter, a void volume of between 80 and about 120 centimeters per gram of web while under a pressure of 689 dynes per square centimeter, a permeability of about 8,000 to about 15,000 darcy, a porosity of at least 95 percent, a surface area per void of 10 to 25 square centimeters per cubic centimeter and a compression resilience in both the wet and dry state of at least about 60 percent. In still further aspects, the thermoplastic fibers comprise at least one of polyolefins, polyesters, polyamides, orlon, acetates or polyvinyl alcohol. In yet further aspects, the disposable urinary incontinence device further comprises an additional non-absorbent layer, wherein the additional non-absorbent layer is adjacent a planar surface of the liquid-stable resilient member. In still further aspects, the elongated member has a tubular profile along a longitudinal axis. In yet further aspects, the elongated member comprises an end seal at the first end and at the second end, each of which is substantially free of the resilient member. In still further aspects, the disposable urinary incontinence device comprises a fold guide in the form of an embossment disposed on the cover sheet. In yet further aspects, the cover sheet comprises at least one of polyethylene or polypropylene. In still further aspects, the cover sheet is hydrophobic. In yet further aspects, the disposable urinary incontinence device comprises a first aperture adjacent the first end of the elongated member and a second aperture adjacent the second end of the elongated member, wherein the first aperture and the second aperture are substantially aligned in the W-shaped profile-folded elongated member. In still further aspects, the first aperture is located from 2 mm to 20 mm from the first end and the second aperture is located from 2 to 20 mm from the second end. In yet further aspects, the disposable urinary incontinence device comprises a withdrawal member, wherein the withdrawal member is present in both the first aperture and the second aperture. In yet further aspects, the withdrawal member is in the form of a string. In still further aspects, the disposable urinary incontinence device has a transverse device compression from 100 gf to 900 gf, as measured by the Transverse Device Compression Test. In yet further aspects, the disposable urinary incontinence device having a W-shaped profile has been compressed to form a pledget having an insertion end and a trailing end. In still further aspects, the pledget has substantially equivalent wet and dry expansion characteristics. In yet further aspects, the disposable urinary incontinence device comprises an applicator having an insertion end and a trailing end, wherein the pledget is disposed within the applicator such that the insertion end of the pledget is adjacent the insertion end of the applicator. In still further aspects, the applicator comprises: a tapered barrel having an insertion end, a trailing end and an elliptical cross-section profile; a gripping portion having an insertion end, a trailing end and a finger contour; and a hollow plunger having an insertion end, a trailing end, a head flange, a rear flange, a shaft portion, and a substantially race-track cross-section profile; wherein the insertion end of the gripping portion is connected to the trailing end of the barrel; and wherein the head flange and at least part of the shaft portion are disposed within the gripping portion.

In some aspect, a method of making a nonabsorbent disposable device comprises:

a) providing a web of non-absorbent resilient material, b) forming the web of non-absorbent resilient material into the desired cross-sectional shape to form a resilient member, c) covering the resilient member with a non-absorbent cover sheet to form an elongated member having a first end, a second end;

d) folding the elongated member upon itself at first fold region located between the first end and the second end; folding the elongated member a second time at a second fold region disposed between the first end and the first fold region; and folding the elongated member a third time at a third fold region disposed between the second end and the first fold region; forming a first portion located between the first end and the second fold region, a second portion located between the second end and the third fold region, a third portion located between the first fold region and a second fold region, and a fourth portion located between the first fold region and the third fold region; wherein the first portion is substantially aligned adjacent to the second portion, the first portion is substantially aligned adjacent to the third portion, the second portion is substantially aligned adjacent to the fourth portion, and the first portion and the second portion are disposed between and adjacent to the third portion and the fourth portion to form a disposable urinary incontinence device having a W-shaped profile; and e) securing the first portion to the second portion with a withdrawal member.

In further aspects, the method further comprises:

a) providing a first aperture in the first portion;

b) providing a second aperture in the second portion; and c) attaching a withdrawal member in the form of a string to the first portion and the second portion by threading the withdrawal member through both the first aperture and the second aperture. In still further aspects, the method further comprises compressing the disposable urinary incontinence device into a pledget having an insertion end and a trailing end. In yet further aspects, In yet further aspects, the method further comprises:

a) inserting the pledget into an applicator having an insertion end and a trailing end such that the insertion end of the pledget is adjacent the insertion end of the applicator; wherein the applicator comprises: a tapered barrel having an insertion end, a trailing end and an elliptical cross-section profile; a gripping portion having an insertion end, a trailing end and a finger contour; and a hollow plunger having an insertion end, a trailing end, a head flange, a rear flange, a shaft portion, and a substantially race-track cross-section profile; wherein the insertion end of the gripping portion is connected to the trailing end of the barrel; and wherein the head flange and at least part of the shaft portion are disposed within the gripping portion; and b) threading a withdrawal member through the barrel, the gripping portion and the plunger such that a portion of the withdrawal member extends past the rear flange of the plunger.

In some aspects, a method for alleviating female urinary incontinence comprises:

a) providing the disposable urinary incontinence device comprising a liquid-stable resilient member and a cover sheet that envelops the liquid-stable resilient member to form an elongated member having a tubular profile, wherein the elongated member has a first end, a second end, a first fold region disposed between the first end and the second end, a second fold region disposed between the first end and the first fold region, a third fold region disposed between the second end and the first fold region;

b) folding the elongated member at the first fold region, the second fold region and the third fold region to form a first portion located between the first end and the second fold region, a second portion located between the second end and the third fold region, a third portion located between the first fold region and a second fold region, and a fourth portion located between the first fold region and the third fold region to provide an elongated member in a folded condition; wherein the first portion is substantially aligned adjacent to the second portion, the first portion is substantially aligned adjacent to the third portion, the second portion is substantially aligned adjacent to the fourth portion, and the first portion and the second portion are disposed between and substantially adjacent to the third portion and the fourth portion to form a disposable urinary incontinence device having a W-shaped profile;

c) compressing the disposable urinary incontinence device having a W-shaped profile into a compressed pledget having an insertion end and a trailing end;

d) inserting the compressed pledget into a woman's vagina with the insertion end entering first;

e) positioning the compressed pledget within the vagina at a location ranging from the urethral sphincter muscle to the vaginal opening;

f) allowing the compressed pledget to expand within the vagina to form an inserted disposable urinary incontinence device to provide pressure to the urethro-vaginal myofascial area; and e) permitting the urethra to be compressed upon itself.

In further aspects, the method further comprises attaching a withdrawal member to the first portion and the second portion of the elongated member. In still further aspects, the method further comprises inserting the compressed pledget into an applicator having an insertion end and a trailing end. In yet further aspects, the method further comprises gripping the applicator at a gripping portion, inserting the insertion end of the applicator into the vagina through the vaginal opening, and pushing a plunger to eject the compressed pledget from the applicator to form an inserted urinary incontinence device. In still further aspects, the method further comprises adjusting the pressure exerted by the inserted urinary incontinence device by pulling on a withdrawal member while the applicator is disposed within the vagina. In yet further aspects, the method further comprises removing the urinary incontinence device from the vagina by pulling on the withdrawal member.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

FIG. 13A is an elongated member after it has been folded at a first fold region.

FIG. 13B is the folded elongated member of FIG. 13A after a withdrawal member has been attached.

FIG. 13C is the elongated member of FIG. 13B after it has been folded at a second fold region and at a third fold region to form a disposable urinary incontinence device having a W-shaped profile.

FIG. 13D is the disposable urinary incontinence device of FIG. 13C after it has been compressed into a pledget.

FIG. 14B is a side view of the applicator of FIG. 14A in an assembled condition.

FIG. 14C is a side view of the applicator of FIG. 14B rotated 90° about a longitudinal axis.

FIG. 15A is a perspective view of a method of making an elongation member of the present invention.

FIG. 15B is a cross-section view of a radially compressed randomly folded resilient member of FIG. 15A taken at A-A.

Figure 1:
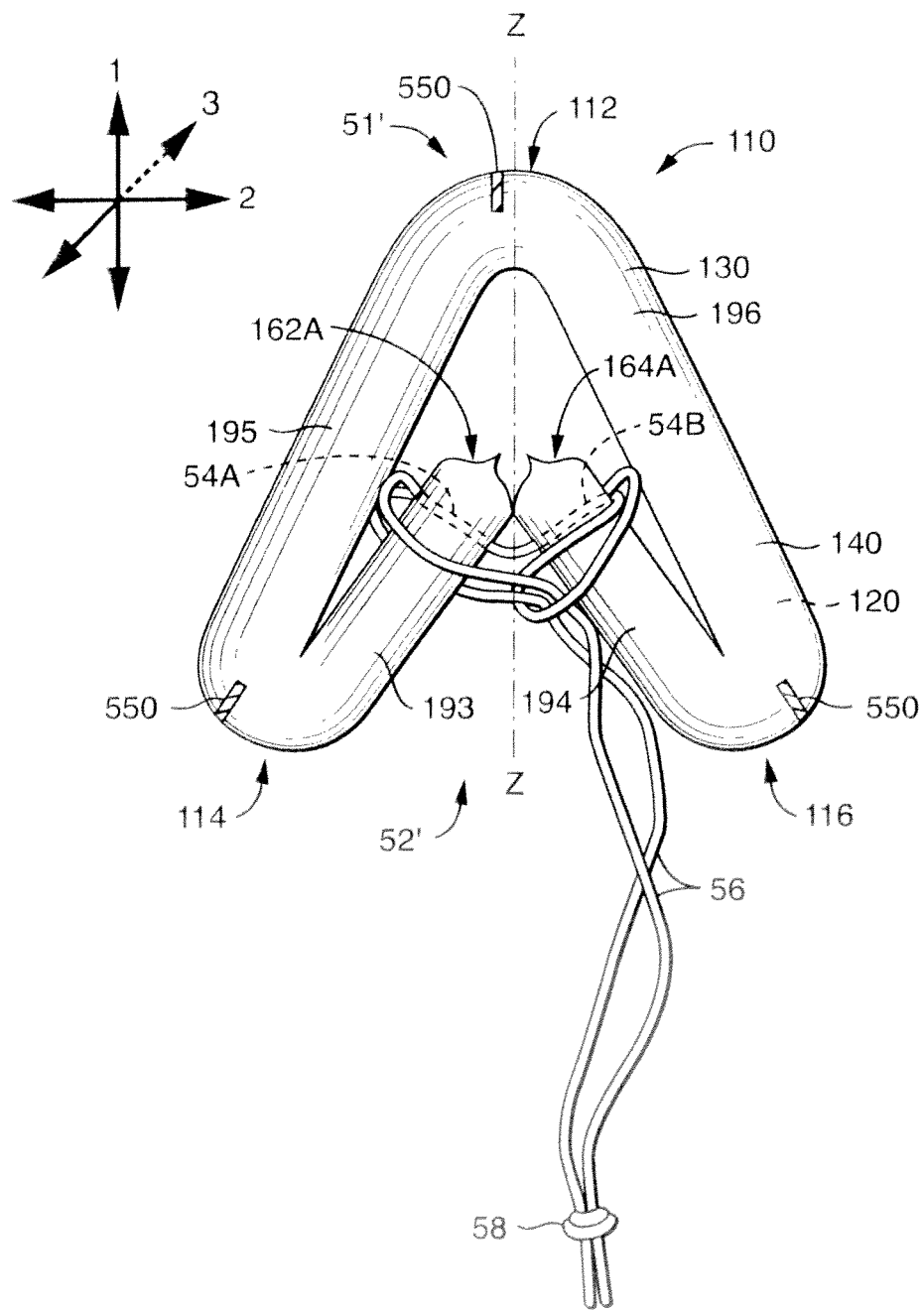
FIG. 1 is a side view of a disposable urinary incontinence device of the present invention.

Repeated use of reference characters in the present specification and drawings is intended to represent the same or analogous features or elements of the present invention. The drawings are representational and are not necessarily drawn to scale. Certain proportions thereof may be exaggerated, while others may be minimized.

TEST METHODS

Unless otherwise noted, all tests are performed at a temperature of 23±2° C. and a relative humidity of 50±5%.

Thickness Test

Figure 17:
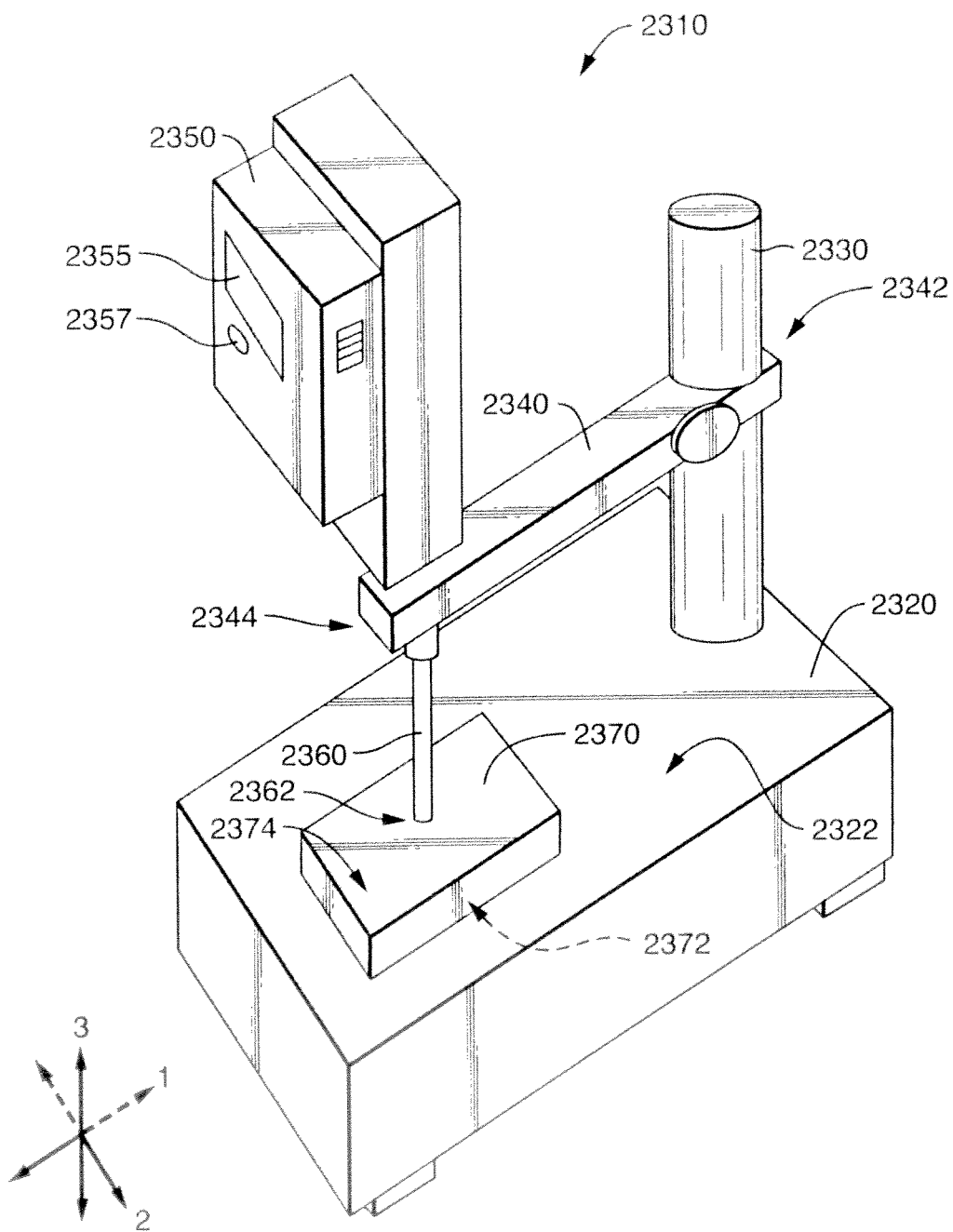
FIG. 17 is a perspective view of a thickness tester utilized in the Thickness Test.

The thickness value of a sample specimen is determined using a thickness tester such as seen in FIG. 17. The thickness tester 2310 includes a granite base 2320 having a clamp shaft 2330 where the top planar surface 2322 of the granite base 2320 is flat and smooth. A suitable granite base is a Starret Granite Base, model 653G (available from The L.S. Starrett Company, having a place of business located in Athol, Mass., U.S.A.) or equivalent. A clamp arm 2340 is secured to the clamp shaft 2330 at one end 2342 of the clamp arm 2340, and a digital indicator 2350 is secured to the clamp arm 2340 at the opposing end 2344. A suitable indicator is a Mitutoyo ID-H Series 543 Digimatic Indicator (available from Mitutoyo America Corp., having a place of business located in Aurora, Ill., U.S.A.) or equivalent. Extending downward from the indicator 2350 is a vertically-movable plunger 2360.

To perform the procedure, a block 2370 having a length of 50 mm and a width of 44 mm is placed onto the planar top surface 2322 of the granite base 2320. The block 2370 is constructed of acrylic and is flat and smooth on at least the planar bottom surface 2372. The thickness and weight of the block 2370 is configured such that the thickness tester 2310 provides a force of 166 $g_f$. Next, the thickness tester 2310 is gently lowered along the clamp shaft 2330 such that the bottom surface 2362 of the plunger 2360 is in direct contact with the longitudinal 1 and transverse 2 center of the planar top surface 2374 of the block 2370, and the plunger length is at approximately 100% in the z-direction 3. The digital indicator 2350 is then tared (i.e., zeroed) by pressing the "zero" button 2357, hereinafter referred to as the "taring step." The digital display 2355 of the digital indicator 2350 should display "0.00 mm" or equivalent.

The block 2370 and plunger 2360 are then raised vertically (z-direction 3) as a unit, and the sample specimen is placed onto the top surface 2322 of the granite base 2320 in the same location that the block 2370 was positioned during the taring step, such that the sample specimen is substantially centered longitudinally 1 and transversely 2 under the planar bottom surface 2372 of the block 2370. The block 2370 and plunger 2360 are then gently lowered as a unit such that the bottom surface 2362 of the plunger 2360 remains substantially centered longitudinally 1 and transversely 2 on the planar top surface 2374 of the block 2370. The planar bottom surface 2362 of the block 2370 should remain parallel to the planer top surface 2322 of the granite base 2320 during measurement. After 3 seconds, the measurement from the digital display 2355 is recorded to the nearest 0.01 mm to provide the thickness of the sample specimen.

Spinning Retention Capacity Test

The Spinning Retention Capacity Test measures the amount of water that a material holds to determine whether the material is considered to be "non-absorbent" as the term is used herein. To perform the procedure, a sample specimen of material is weighed to the nearest 0.1 grams, and the weight is recorded as the Dry Weight. The sample is then completely submerged in tap water having a temperature of 23±2° C. for 10 minutes. If the sample floats, then the sample should be gently pushed and held under the water surface via the tester's fingers, or equivalent (hereinafter referred to as the "saturation step"). After the 10 minute saturation step, the saturated sample is gently removed from the water and is placed into a model no. Model 776SEK-TS SPIN-X spindryer having a diameter of 34.2 cm and a height of 63.5 cm, a weight of 11.3 kg and a wet load capacity of 4.5 kg (available from Spin-X, having a place of business located in Houston, Tex., U.S.A.). The spindryer spins at 3,300 R.P.M. and produces 1,340 G' forces. The spindryer is turned on and allowed to reach maximum speed. Once the maximum speed has been reached, the sample is allowed to spin for 2 minutes, at which point the spindryer is turned off. Once the spindryer has stopped, the sample is gently removed from the spindryer and weighed to the nearest 0.1 gram and is recorded as the Retention Weight. The Spinning Retention Capacity is then calculated in units of grams water per gram material using the following formula:

Retention Wt.−Dry Wt.=Spinning Retention Capacity.

Elongated Member Compression Test

To perform this procedure, an MTS Synergie Model 200 tensile testing machine (or equivalent) equipped with a computer-based control and data acquisition system running MTS TESTWORKS software (available from MTS Corporation, having a place of business located in Eden Prairie, Minn., U.S.A.). A software-deflection-compensated load cell was used for this test. Steel circular compression platens were attached to the load cell (upper platen) and the base of the tensile machine (lower platen) (available from Instron Worldwide, having a place of business located in Norwood, Mass., U.S.A., or equivalent). The upper platen had a diameter of 19 mm, and the lower platen had a diameter of 88.9 mm. Both platens had flat, smooth finishes, and provision was made to align both platen contact surfaces such that there was no more than a 0.005 inch (0.0127 centimeter) gap between any point on the contact surface of the upper platen and the lower platen when the two platens were brought into physical contact at any other point when mounted on the tensile machine. The load cell was properly calibrated according to the manufacturer's instructions (including necessary warm-up periods) and was zeroed with the platens attached.

After the platens were properly installed and aligned, the platens were carefully brought together and loaded to a pressure of 20 kPa. At this point, the elongation channel of the tensile machine was zeroed. The tensile machine was then backed-off exactly 2 cm under software control and the elongation channel was re-zeroed. This left the platen spacing at 2 cm when the tensile frame elongation channel read zero. All subsequent separation measurements were made based on programmed software calculations that corrected for this 2 cm offset between actual platen spacing and elongation channel reading. (Use of an offset is a safety precaution known to those skilled in the art; it prevents platen crashing if a machine operator accidentally sends the tensile machine to the 'home' position.)

A compression test was initiated by carefully centering a single elongated member having a length and diameter equal to, or greater than, the diameter of the upper platen onto the lower platen. The tensile machine crosshead was then manually moved to a position slightly above the elongated member and the test was run through the TESTWORKS software. This test routine compressed the elongated member to a pressure of 20 kPa at a speed of 1 cm per minute. Immediately upon achieving the 20 kPa pressure, the tensile frame reversed direction and released compression. The reverse speed was also 1 cm per minute. This completed the test. Data was recorded for both the compression and the rebound portions of the test to allow subsequent calculation of results. The TESTWORKS software automatically performed the pertinent calculations, providing Energy Loading (g-cm), Energy Uploading (g-cm) and Hysteresis Loss (%).

Transverse Device Compression Test

Figure 18:
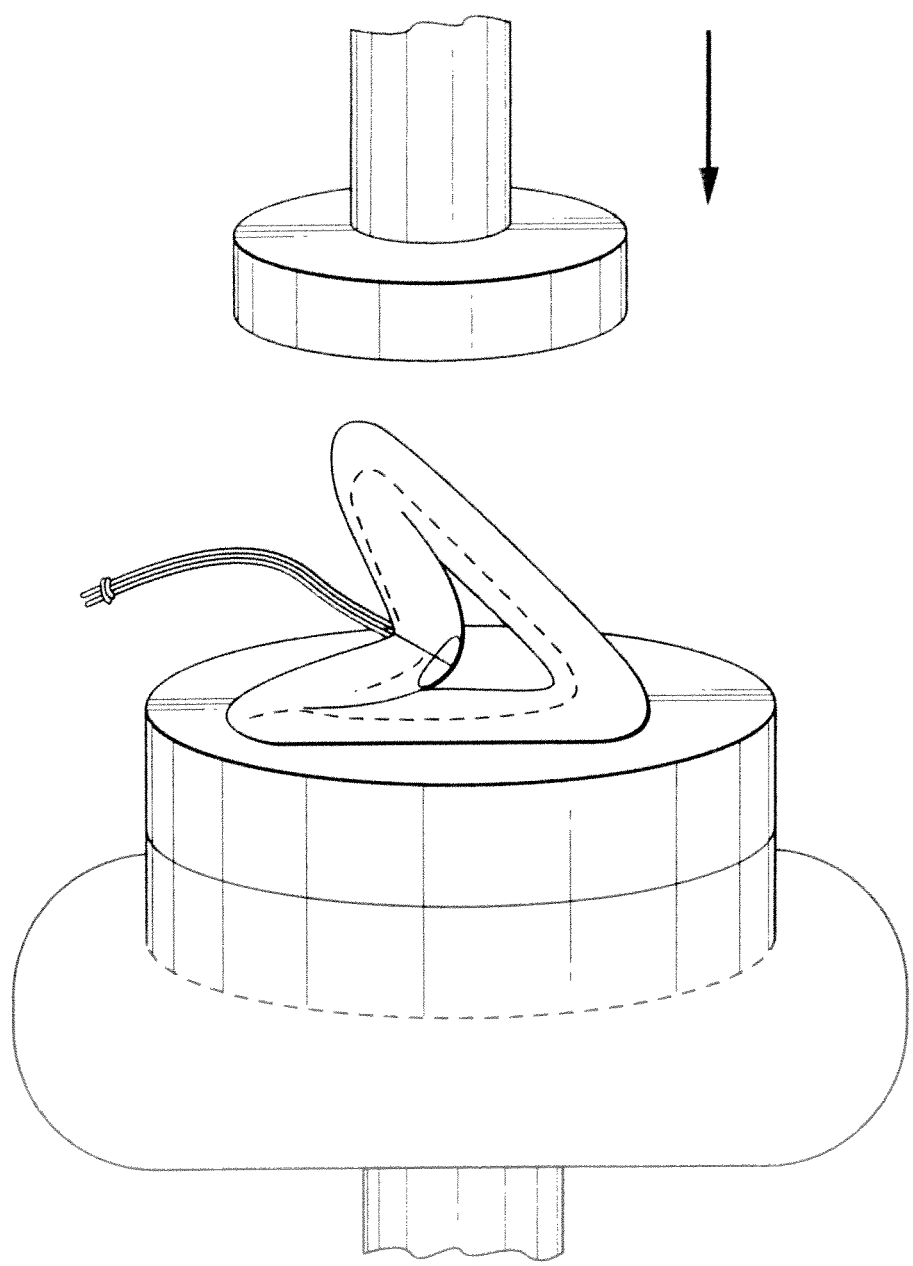
FIG. 18 is a perspective view showing a partial section of a compression tester utilized for the Compression Test having a disposable urinary incontinence device disposed thereon.

The Transverse Device Compression Test measures the compression properties of the urinary incontinence device as a whole in the transverse 2 direction, such as shown in FIG. 18. To perform this procedure, an MTS Synergie Model 200 tensile testing machine (or equivalent) equipped with a computer-based control and data acquisition system running MTS TESTWORKS software (available from MTS Corporation, having a place of business located in Eden Prairie, Minn., U.S.A.). A software-deflection-compensated load cell was used for this test. Steel circular compression platens were attached to the load cell (upper platen) and the base of the tensile machine (lower platen) (available from Instron Worldwide, having a place of business located in Norwood, Mass., U.S.A., or equivalent). The upper platen had a diameter of 57.2 mm, and the lower platen had a diameter of 88.9 mm. Both platens had flat, smooth finishes, and provision was made to align both platen contact surfaces such that there was no more than a 0.005 inch (0.0127 centimeter) gap between any point on the contact surface of the upper platen and the lower platen when the two platens were brought into physical contact at any other point when mounted on the tensile machine. The load cell was properly calibrated according to the manufacturer's instructions (including necessary warm-up periods) and was zeroed with the platens attached.

After the platens were properly installed and aligned, the platens were carefully brought together and loaded to a pressure of 20 kPa. At this point, the elongation channel of the tensile machine was zeroed. The tensile machine was then backed-off 7.62 cm under software control and the elongation channel was re-zeroed. This left the platen spacing at 7.62 cm when the tensile frame elongation channel read zero. All subsequent separation measurements were made based on programmed software calculations that corrected for this 7.62 cm offset between actual platen spacing and elongation channel reading. (Use of an offset is a safety precaution known to those skilled in the art; it prevents platen crashing if a machine operator accidentally sends the tensile machine to the 'home' position.)

A compression test was initiated by carefully centering a incontinence device onto the lower platen. The tensile machine crosshead is then manually moved to a position slightly above the incontinence device and the test was run through the TESTWORKS software. This test routine compressed the elongated member at a speed of 12.7 cm per minute to a distance of 2.5 cm from the top platen to the lower platen. The compression is expressed in $g_f$.

Resiliency Test

This test measures the resiliency of a sample specimen. The thickness of the sample is first measured under a force of 166 $g_f$ for 3 seconds to obtain the Initial Thickness of the sample. A force of 11 $kg_f$ is then applied to the sample using suitable means for 30 seconds and the thickness is measured as the Compressed Thickness. The 11 kgf is then removed and the sample is allowed to expand for 5 minutes. After the 5 minutes, the thickness of the sample is again measured under a force of 166 $g_f$ for 3 seconds to obtain the Final Thickness. Suitable means for measuring the thickness include the Thickness and the Elongated Member Compression Test described above, or equivalent, modified appropriately to fulfill the requirements of this Resiliency Test. The Resilient Compression and the Resilient Expansion are then calculated using the following formulas:

Resilient Compression (%)=[(Initial Thickness (mm)−Compressed Thickness (mm)/Initial Thickness (mm)]×100%

Resilient Expansion (%)=Final Thickness (mm)/Initial Thickness (mm)

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements.

The term "bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements.

The term "disposable" is used herein to describe absorbent articles that are not intended to be laundered or otherwise restored or reused as an absorbent article after a single use.

The terms "elastic," "elasticized," "elasticity," and "elastomeric" mean that property of a material or composite by virtue of which it tends to recover its original size and shape after removal of a force causing a deformation. Suitably, an elastic material or composite can be elongated by at least 50 percent (to 150 percent) of its relaxed length and will recover, upon release of the applied force, at least 40 percent of its elongation.

The term "fiber" refers to a continuous or discontinuous member having a high ratio of length to diameter or width. Thus, a fiber may be a filament, a thread, a strand, a yarn, or any other member or combination of these members.

The term "hydrophilic" describes materials which are wetted by aqueous liquids in contact with the materials. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, materials having contact angles less than 90 degrees are designated "wettable" or hydrophilic, and fibers having contact angles greater than 90 degrees are designated "nonwettable" or "hydrophobic".

The term "join" and its derivatives refer to the connecting, adhering, bonding, attaching, sewing together, or the like, of two elements. Two elements will be considered to be joined together when they are integral with one another or joined directly to one another or indirectly to one another, such as when each is directly joined to intermediate elements.

The term "liquid impermeable," when used in describing a layer or multi-layer laminate means that liquid, such as urine, menses or bowel movement, will not pass through the layer or laminate, under ordinary use conditions, in a direction generally perpendicular to the plane of the layer or laminate at the point of liquid contact.

The term "liquid permeable" refers to any material that is not liquid impermeable.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded-carded-web processes. The basis weight of nonwoven fabrics is usually expressed in ounces of material per square yard (osy) or grams per square meter (gsm) and the fiber diameters are usually expressed in microns.

The term "urinary incontinence device" refers to a device which is inserted into the vagina to treat urinary incontinence.

The term "thermoplastic" describes a material that softens when exposed to heat and which substantially returns to a non-softened condition when cooled to room temperature.

The term "vaginal liquid" refers to aqueous liquids, including viscoelastic liquids, pertaining primarily to those liquids that are present in the vaginal canal, including water, sweat, urine, blood, menses and mucin.

These terms may be defined with additional language in the remaining portions of the specification.

DETAILED DESCRIPTION

Figure 3:
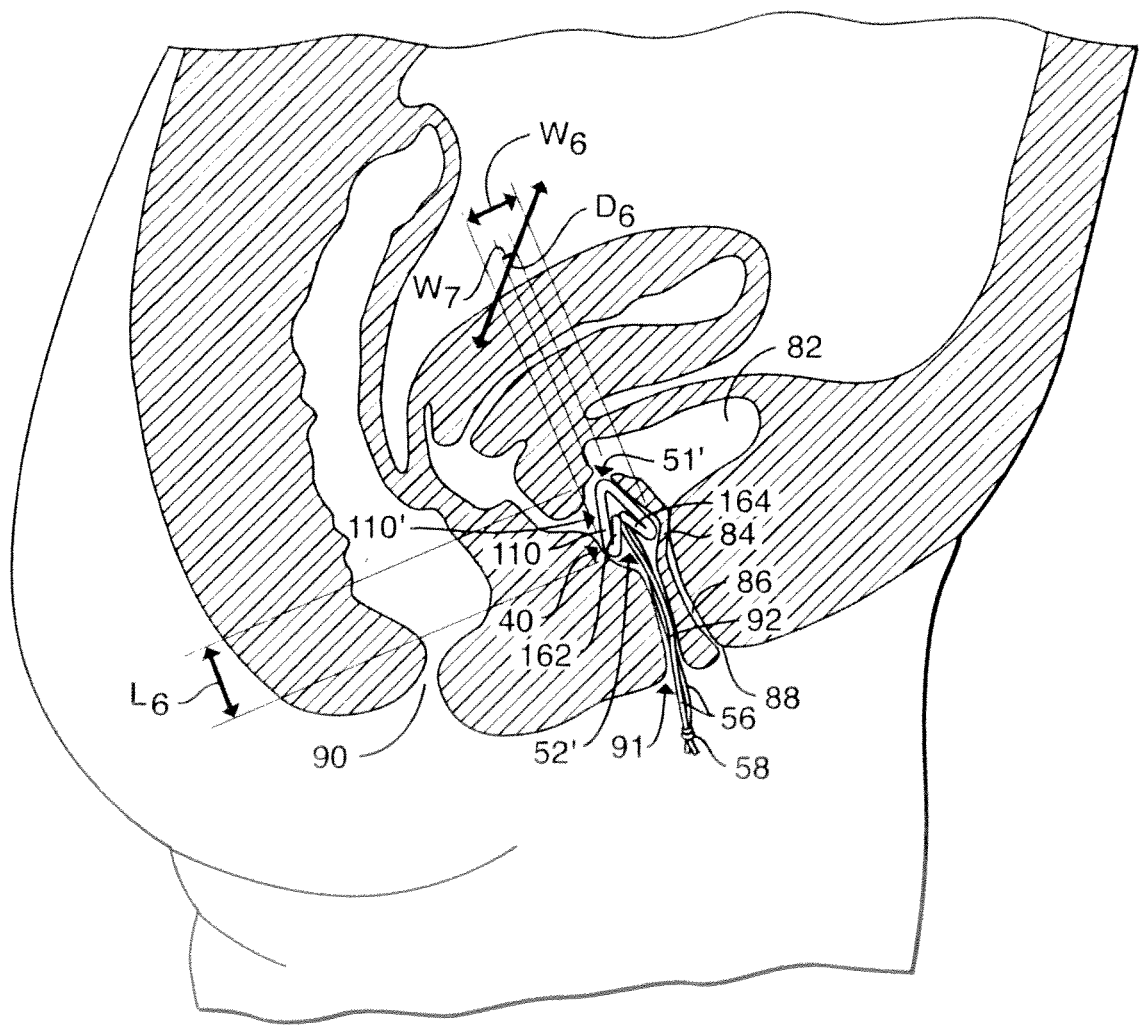
FIG. 3 is a mid-sagittal section of a human torso showing the expandable W-shaped urinary incontinence device positioned in the vagina adjacent to the urinary sphincter muscle and expanded to provide support for the musculature and tissue near the urethro-vaginal myofascial region and the urethra.
Figure 4:
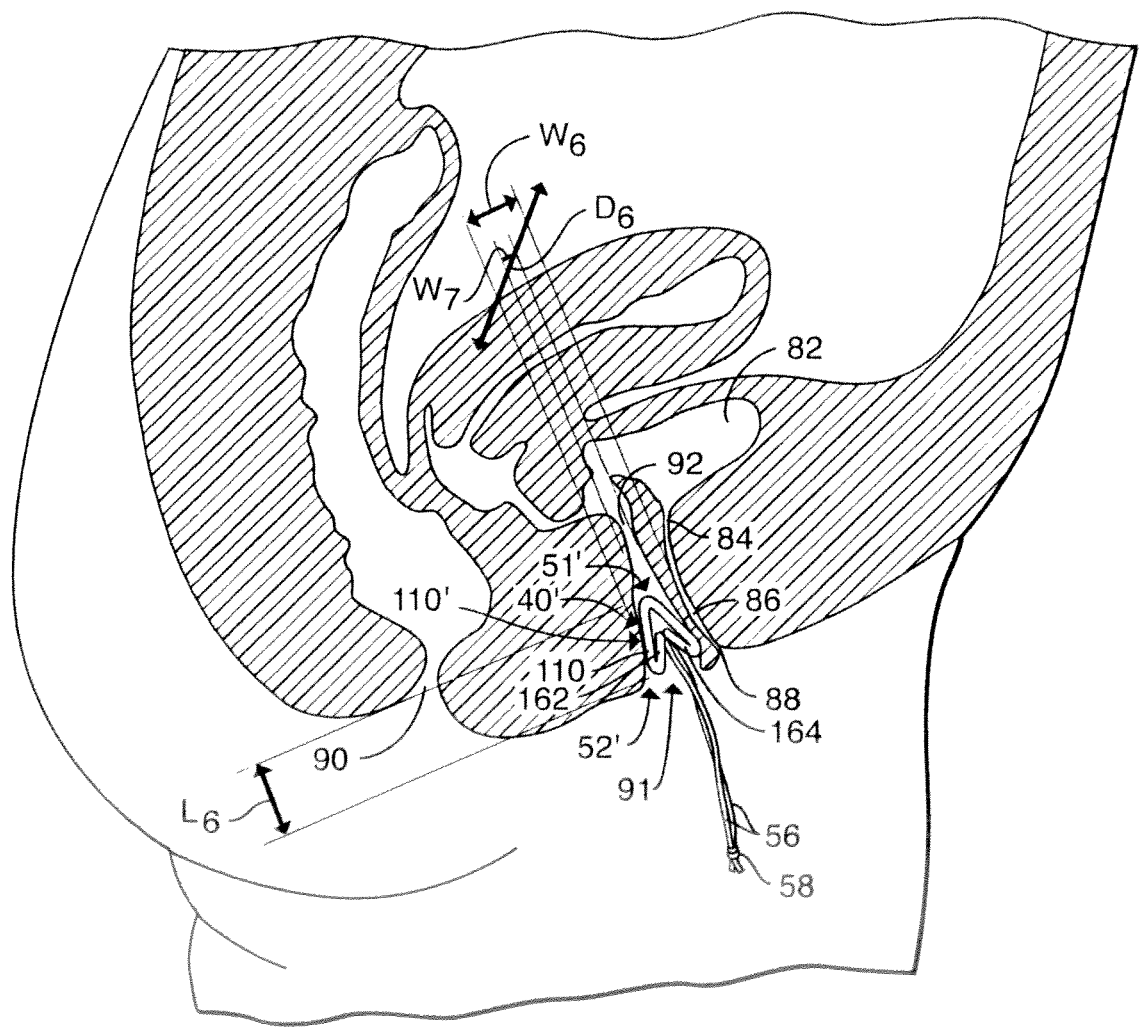
FIG. 4 is a mid-sagittal section of a human torso showing the expandable W-shaped urinary incontinence device positioned near the vaginal opening and expanded to provide support for the musculature and tissue near the urethro-vaginal myofascial region and the urethra.

FIGS. 3 and 4 illustrate a cross section of a woman's vaginal cavity 92. A woman's urethra 88 is located adjacent to and anterior to the vagina 92. The woman's anus 90 is located on the posterior side of the vagina 92. The urethra 88 is a conduit for removing urine which has accumulated in the woman's bladder 82 to an external orifice located at the lower end of the urethra 88. Between the vagina 92 and the urethra 88 is the urethro-vaginal myofascial area 86. This area 86 is made up of musculature and body tissue and the body tissue is extremely pliable. The vagina 92 contains a plurality of rugosities (not shown) which line its inside walls. The rugosities consist of wrinkles or creases in the body tissue which allows for expansion and contraction of the side walls of the vagina 92. A urinary sphincter muscle 84 is situated at the upper portion of the urethra 88 adjacent to the bottom surface of the bladder 82. The sphincter muscle 84 operates to prevent the involuntary loss of urine. However, after birthing and/or with age, or for other various reasons, the pelvic floor muscles can begin to sag and the cross-sectional configuration of the sphincter muscle can change from a circular profile to a non-circular profile. Such a change increases the likelihood that a woman will experience involuntary urine loss, including stress-induced urinary incontinence caused by sneezing, laughing, coughing, lifting, standing-up, and the like.

Disposable urinary incontinence devices of this invention are useful in the control of stress induced urinary leakage. The disposable urinary incontinence device of the present invention can have a liquid-stable resilient member, and can additionally include a cover sheet, where the liquid-stable resilient member can be at least partially wrapped by the cover sheet.

To gain a better understanding of the present invention, attention is directed to FIGS. 1-4 for exemplary purposes showing a disposable urinary incontinence device 110 of the present invention. The device 110 is designed to be folded, compressed and inserted into a woman's vagina 92, and then allowed to expand so as to relieve or eliminate the involuntary passage of urine through the urethra 88 from the bladder 82. In general, the expansion of the device 110, including spontaneously de-compressing and/or unfolding, can provide pressure to the musculature and body tissue located near the urethro-vaginal myofascial area, causing the urethra 88 to be compressed upon itself during episodes of increased intra-abdominal pressure. In addition, the expansion of the device 110 in the vagina 92 will assist the urinary sphincter muscle 84 in maintaining a circular cross-sectional configuration. When this circular cross-sectional configuration is maintained, the sphincter muscle 84 can close properly and decrease the tendency for the involuntary escape of urine due to stress urinary incontinence.

Figure 5:
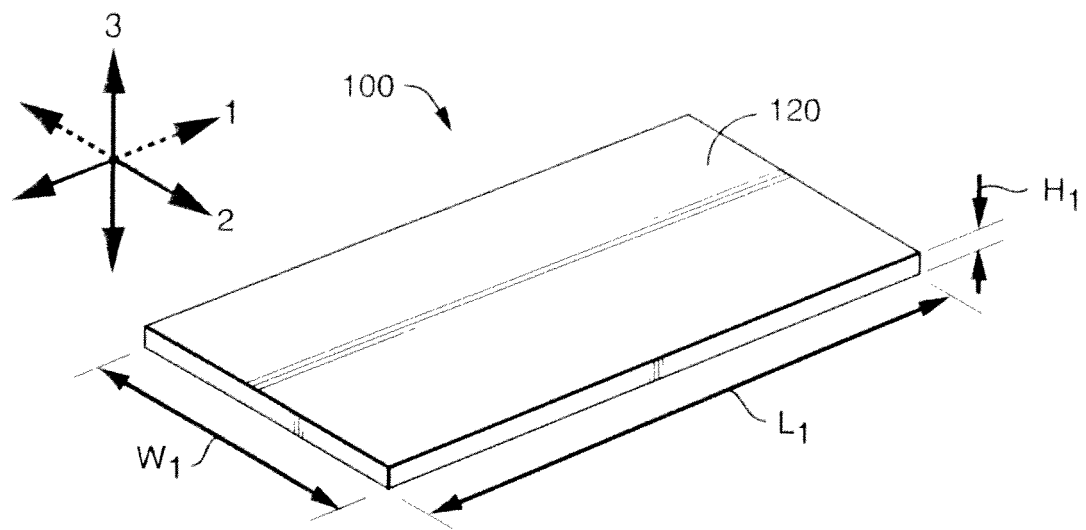
FIG. 5 is a perspective view of a starting structure used to form the disposable urinary incontinence device of the present invention.
Figure 6:
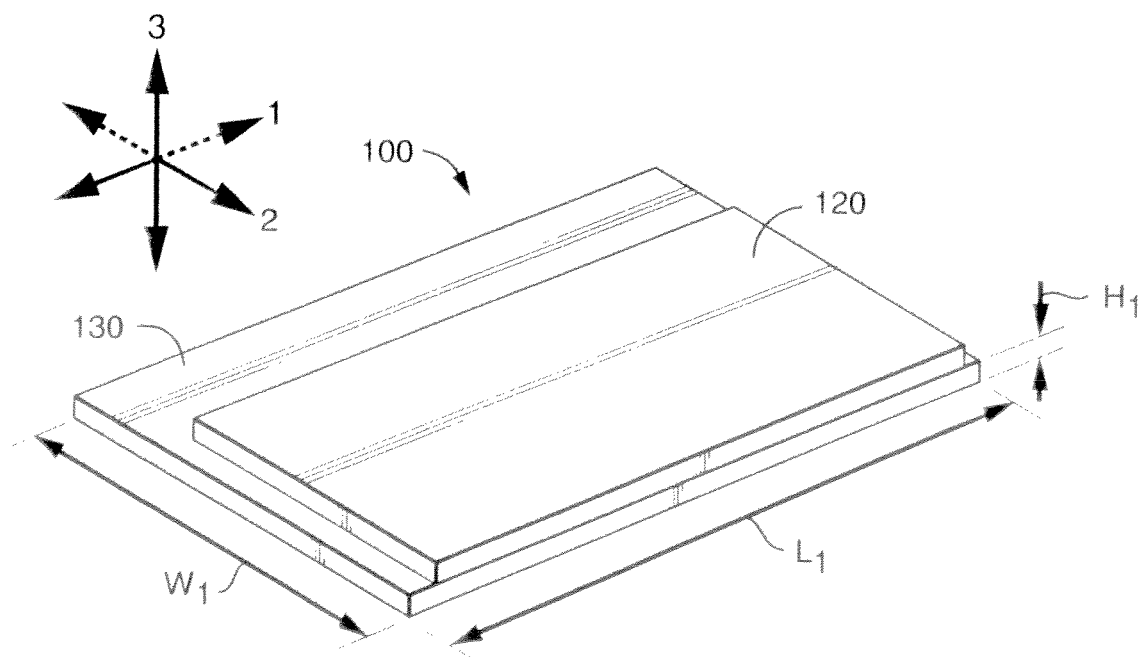
FIG. 6 is a perspective view of a starting structure used to form the disposable urinary incontinence device of the present invention.
Figure 7:
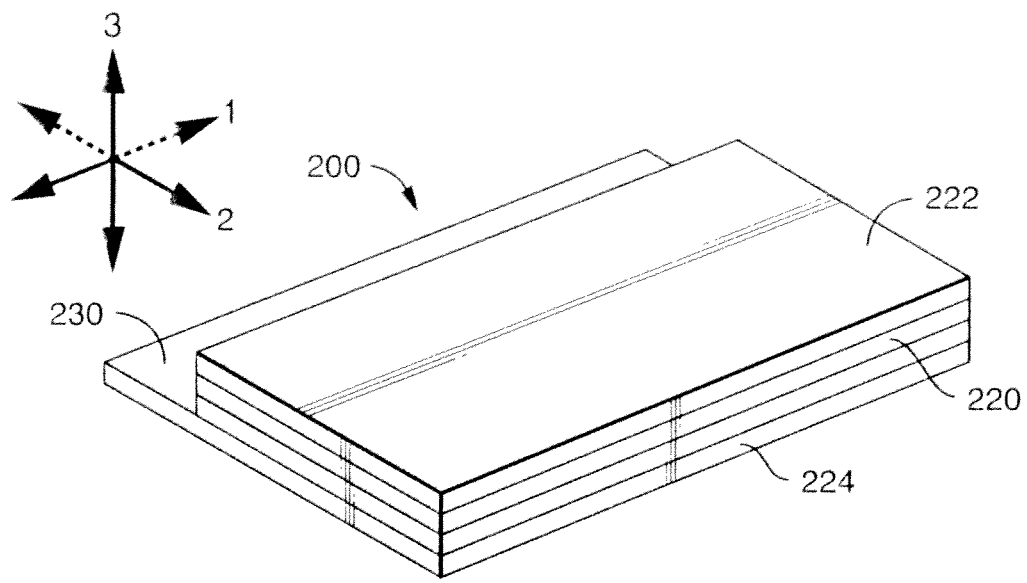
FIG. 7 is a perspective view of a starting structure used to form the disposable urinary incontinence device of the present invention.

Referring to FIGS. 5-7, the disposable device 110 includes a liquid-stable resilient member 120. In additional aspects as described below, the urinary incontinence device 110 may also include additional layers, as well as a cover sheet.

FIG. 5 illustrates an exemplary starting structure 100 for constructing the disposable urinary incontinence device comprising a single liquid-stable resilient member 120. The resilient member 120 is desirably liquid-stable when exposed to aqueous fluids, such as vaginal fluids. As used herein, the term "liquid-stable" refers to a material, member or device that is capable of maintaining equivalent dimensions whether in a dry state or in a wetted state, such as when exposed to aqueous liquids. As used herein, the term "resilient" refers to a material which, after being exposed to an external force (e.g., bending, stretching or compressing), returns to or resumes at least 60% of its original shape or thickness held prior to being exposed to the external force. By way of example, external forces can be applied to the device 110 via mechanical means such as prior to, or during, insertion into the vagina 92, and can be applied to the device 110 after insertion into the vagina, such as by sneezing, coughing, laughing, lifting and the like.

The resilient member 120 can comprise natural or synthetic materials. Suitable natural materials include natural rubber and wool, for example. Suitable synthetic materials include polyolefins, polyethylene, polypropylene, polyester, polybutylene, polyurethane, latex, silicone elastomerics, polyethylene oxide (PEO), polyvinyl alcohol (PVA), rayon, spun cellulose, LYCRA, KEVLAR, carbon fibers and the like. LYCRA and KEVLAR are available from E. I. DuPont de Nemours & Company, having a place of business located in Wilmington, Del., U.S.A. One particular exemplary material suitable for constructing the resilient member includes CHISSO ESC bicomponent fiber (available from Chisso Corporation having a place of business located in New York, N.Y., U.S.A.) which consist of a polypropylene core surrounded by a polyethylene sheath. Other bicomponent fibers made from polypropylene, polyethylene, etc. are commercially available from suppliers such as Exxon and Dow Chemical, as well as from other vendors. Another particular exemplary material suitable for constructing the resilient member includes VOLARA, a polyethylene closed-cell foam available from Voltex, a Division of Sekisui America Corporation having a place of business located in Lawrence, Mass., U.S.A. Another particular exemplary material suitable for constructing the resilient member includes a surge material. Such surge material comprises a plurality of thermoplastic fibers that are heated to form a lofty nonwoven web. The surge material can have a basis weight of at least 85 grams per square meter, a void volume of between 20 and 50 cubic centimeters per gram of web while under a pressure of 3447 dynes per square centimeter (0.05 psi, 345 Pascal), a permeability of about 2,500 to 10,000 Darcy, a porosity (web openness) of at least 95%, a surface area per void of 25 to 60 square centimeters per cubic centimeter and a compression resilience in both the wet and dry state of at least about 60%. Suitable surge materials include Textor Surge 4.25 and Textor Surge 5.25, available from Kimberly-Clark Corporation, having a place of business located in Neenah, Wis., U.S.A.

In some aspects, the resilient member can also be non-absorbent. As used herein, the term "non-absorbent" refers to a material that has a retention capacity of less than 0.3 grams water per gram material, such as less than 0.2 grams, or between 0.3 grams-0.05 grams, as measured by the Spinning Retention Capacity Test. In one example, Textor Surge 4.25 having a basis weight of 150 gsm exhibited a retention capacity of 0.16 g/g, and in another example, Textor Surge 5.25 having a basis weight of 150 gsm exhibited a retention capacity of 0.21 g/g, as measured by the Spinning Retention Capacity Test.

In some aspects, the resilient member can have a Resilient Compression value from about 60% to about 90%, and a Resilient Expansion of between 60% and 100%, as measured by the Resiliency Test. In one example, Textor Surge 5.25 having a basis weight of 150 gsm exhibited a Resilient Compression of 81% and a Resilient Expansion of 82%, as measured by the Resiliency Test.

The resilient member 120 desirably has substantially equivalent dry and wet expansion characteristics. In other words, the resilient member 120 should be made from a material that is capable of returning 220 back to at least about 60% of its original configuration in a dry state, a wet state or in a semi-dry-wet state, such as at least about 70%, or at least about 80% or more, such as 100%. Dry expansion of the urinary incontinence device 110 is beneficial in that the device does not have to be wetted by aqueous liquids, such as vaginal liquids, before the resilient member 120 is capable of expanding within the vagina, and further that the device 110 is not inhibited from returning to at least 60% of its original configuration when wetted by aqueous liquids.

In FIG. 5, the resilient member 120 is depicted as rectangular in the transverse 2 cross-section. However, the resilient member 120 can have a square, circular, oval, or any other desired transverse cross-sectional configuration. In some aspects, the resilient member 120 will have a uniform thickness and width; however, the dimensions of the resilient member 120 do not have to be uniform.

In the illustrated embodiment, the resilient member 120 has a length $L_1$ in the longitudinal direction 1, a width $W_1$ in the transverse direction 2, and a height $H_1$ in the z-direction 3. By way of example only, in some aspects, the length $L_1$ can range from about 127 mm to about 254 mm, such as about 152 mm to about 229 mm, or about 178 mm to about 203 mm; the width $W_1$ can range from about 76 mm to about 203 mm, such as about 102 mm to about 178 mm, or about 127 mm to about 152 mm; and the height $H_1$ (as measured by the Thickness Test) can range from about 1 mm to about 20 mm, such as about 3 mm to about 10 mm, or about 5 mm to about 8 mm.

Figure 8:
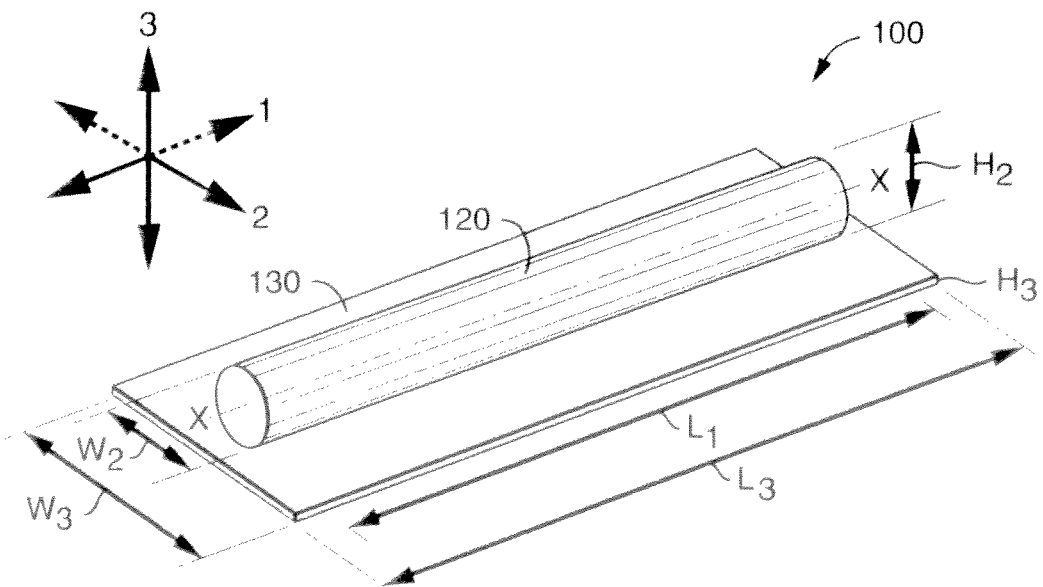
FIG. 8 is a perspective view of a starting structure used to form the disposable urinary incontinence device of the present invention comprising a tubular shaped resilient member and a cover.

In some aspects, the resilient member 120 can be provided as a tubular structure 122 such as shown in FIG. 8, or can be folded, rolled, radially compressed or the like to form such a tubular structure 121, such as seen in FIGS. 10A-11C. When in the form of a tubular structure 121, the resilient member 120 can define a length $L_1$ as set forth above, a width $W_2$ and a height $H_2$. By way of example only, in some aspects, the resilient member 120 in the form of a tubular structure 121 can have a width $W_2$ of about 10 mm to about 40 mm, such as about 10 mm to about 30 mm, or about 10 mm to about 20 mm, and a height $H_2$ of about 10 mm to about 40 mm, such as about 10 mm to about 30 mm, or about 10 mm to about 20 mm. More folds will generally result in a wider resilient member.

The disposable urinary incontinence device 110 of the present invention can also include a cover sheet 130 configured to partially or fully envelop the resilient member 120. The cover sheet 130 can be liquid-permeable or liquid-impermeable. For example, when the cover sheet is liquid-impermeable, it serves to block body fluids from contacting any materials disposed within the cover sheet 130. However, since the resilient member 120 is moisture-stable, it is not necessary that the cover sheet be liquid-impermeable. The cover sheet 130 can provide a smooth outer surface which may or may not be chemically treated to facilitate insertion and/or removal into and out of a woman's vagina. Suitable cover sheet materials include polyolefins such as spunbonds and bonded-carded webs, polyesters, polyethylene, polypropylene, silicon, polystyrene, polyurethane and the like. In some aspects, the surface of the cover sheet 130 can include apertures and/or can be embossed with grooves, dimples, dots and the like that can reduce the surface contact area when inserted into the vagina. In some aspects, a surface treatment that forms a coating on the cover sheet 130, such as mineral oil, may be used to reduce the friction between the device 110 and the labial tissue over time.

FIGS. 6 and 8 illustrate a starting structure 100 comprising a resilient member 120 located above and adjacent to a cover sheet 130. Although the cover sheet 130 can be substantially coextensive with the resilient member 120, the cover sheet 130 can alternately have a width $W_3$ which can be different than the width $W_1$ of the resilient member 120 and/or a length $L_3$ which can be different than the length $L_1$ of the resilient member 120. The thickness $H_3$ of the cover sheet can range from between about 0.1 mm to about 5 mm, such as between about 0.2 mm and about 1 mm, or between about 0.3 mm and about 0.7 mm.

Figure 12:
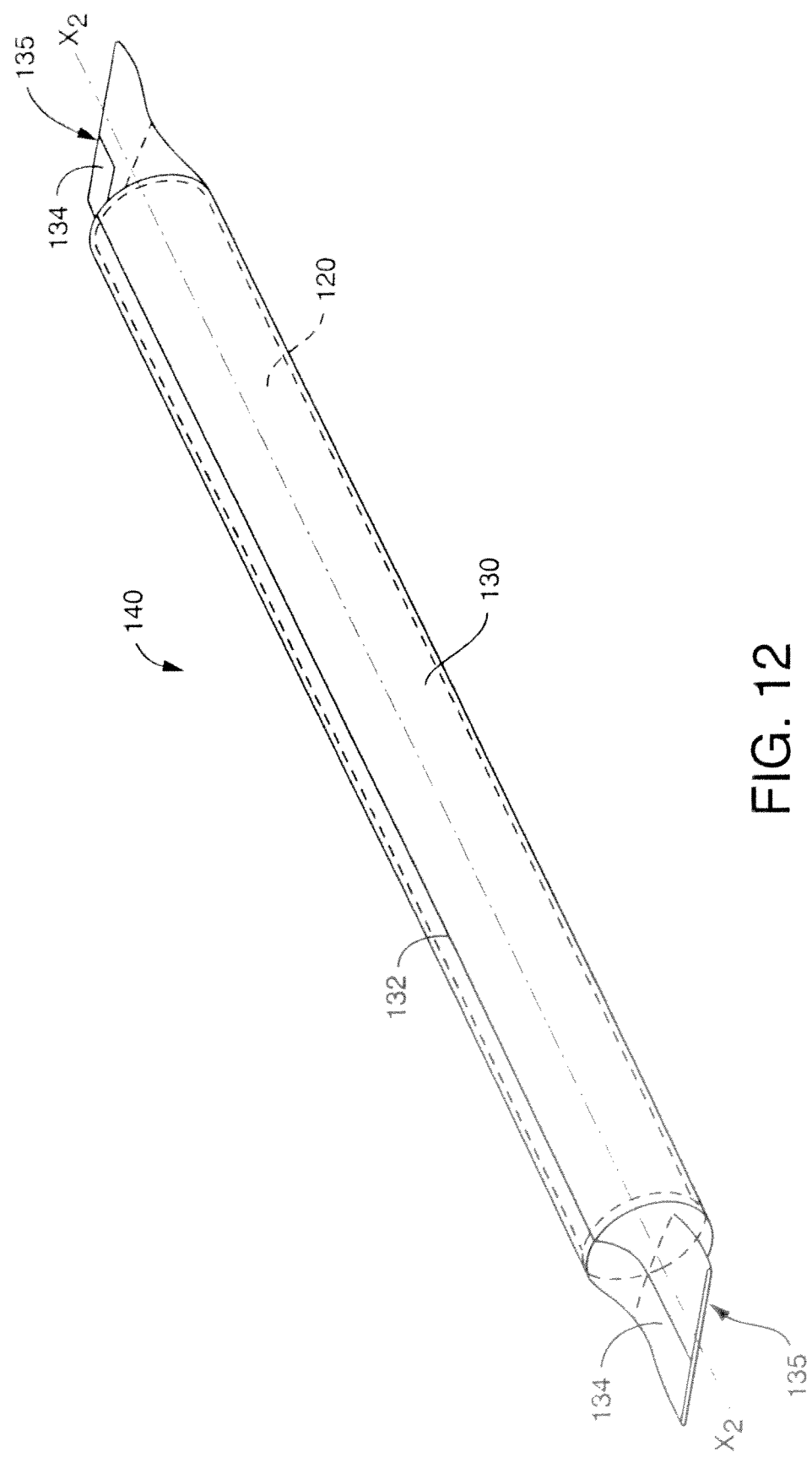
FIG. 12 is a perspective view of an elongation member with a longitudinal seam and sealed end portions.

In aspects where the cover sheet 130 has a greater width than the resilient member 120, the greater dimension for the width $W_2$ allows the cover sheet 130 to be folded over upon itself and be bonded to itself to form a longitudinal bond 132, such as shown in FIG. 12. Suitable bonding means include those well-known in the art, such as by heat, pressure, ultrasonic, adhesive and the like. In some aspects, the cover sheet 130 may be simply folded over upon itself.

In aspects where the cover sheet 130 has a greater length $L_3$ than the resilient member 120, the greater dimension for the length $L_3$ allows the cover sheet 130 to be to be sealed at the ends in a region that may or may not be devoid of resilient material to form an end seal 134 that is substantially free of resilient material, as shown in FIG. 12.

In some aspects, the device 110 of the present invention can also include additional layers. For example, FIG. 7 illustrates a starting structure 100 of a urinary incontinence device 110 an optional first additional layer 122 and an optional second additional layer 124. The additional layers 122,124 can each be located above and adjacent to the resilient member 120 and/or below and adjacent to the resilient member in the z-direction 3. Although two optional layers are illustrated, any number of additional layers can be included in the device 110. Each additional layer, if present, can desirably be liquid-stable and may or may not be attached to the resilient member 120. Suitable materials for any additional layers can include, but is not limited to, those materials that are suitable for the resilient member, or can comprise a beneficial additive, including pH buffering for the skin, vaginal health-care for a female, odor control, coating materials for skin health, or even medicines.

The additional layers 122,124 can, although not necessarily, be sized and arranged to be substantially coextensive with the resilient member or with each other. As used herein, the phrase "substantially coextensive" means that the individual layers have either the same or about the same length and width dimensions; however, some minor dimensional variations may be present. For instance, the width of the layers may vary slightly so that when folded (e.g., FIGS. 10A-11C), the edges of the layers will be substantially flush.

Figure 9A:
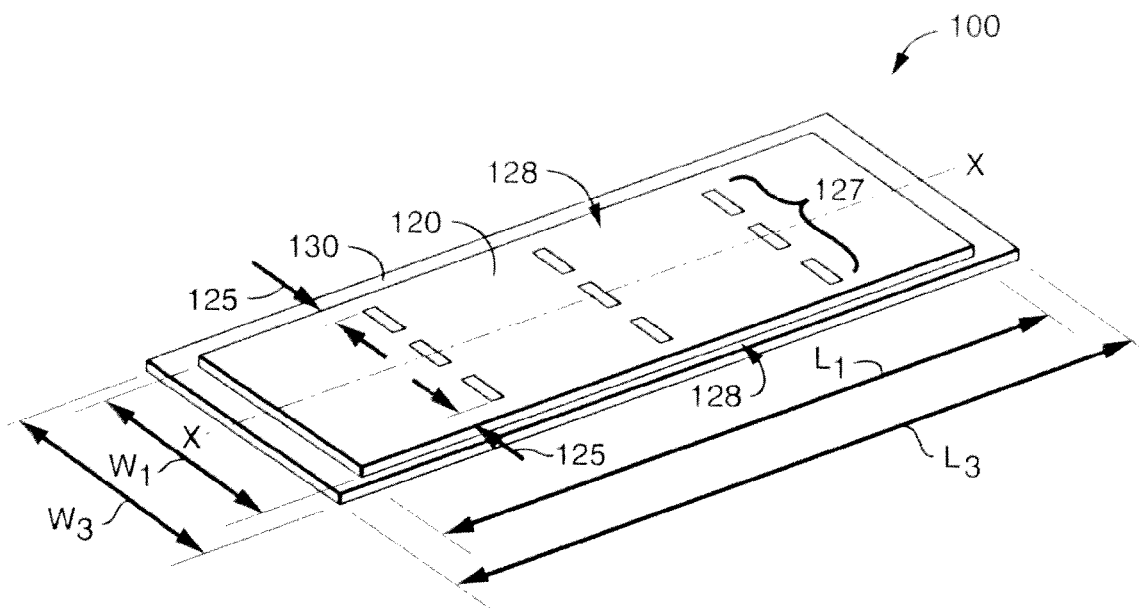
FIG. 9A is a perspective view of a starting structure used to form the disposable urinary incontinence device of the present invention comprising a resilient member having a shaping embossment.
Figure 9B:
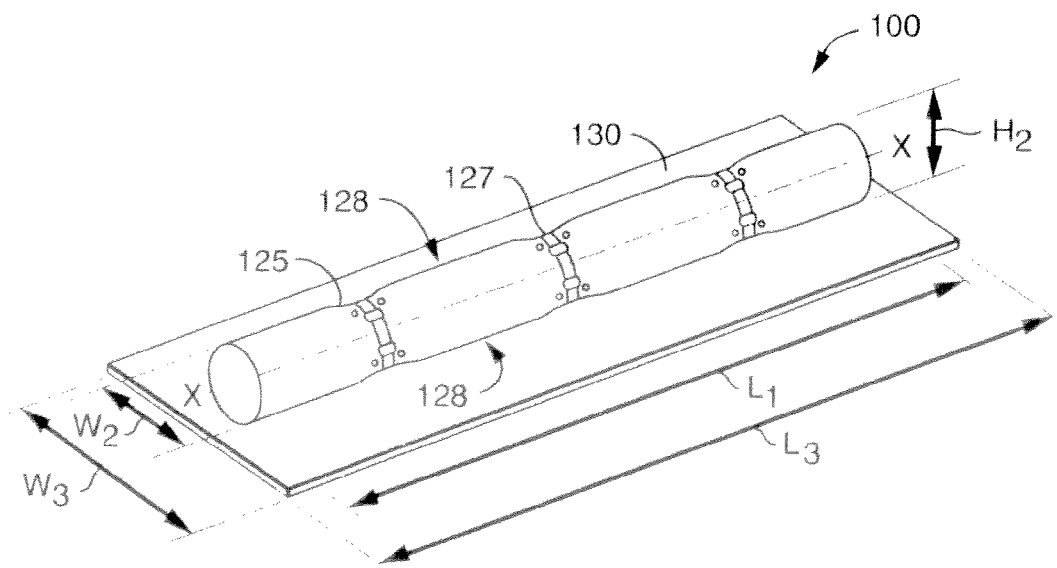
FIG. 9B is a perspective view of a starting structure used to form the disposable urinary incontinence device of the present invention comprising a tubular resilient member having a shaping embossment.

FIGS. 9A and 9B illustrate another aspect of the invention where the resilient member 120 includes a shaping embossment 127 in the transverse direction 2. The shaping embossment 127 can help provide fold regions 112, 114 and 116 for shaping the disposable urinary incontinence device 110, discussed in greater detail below. In some aspects, the shaping embossment 127 is positioned within lateral edges 128 of the resilient member 120. The shaping embossment 127 can have a transverse dimension 125 that is less than the width $W_1$, $W_2$ of the resilient member, such as less than 10 mm from the edges 128, or less than 5 mm from the edges 128, or less than 2 mm from lateral edges 128, or 0 mm from lateral edges 128, or less than between 2 mm and 10 mm from the edges 128.

Figure 10A:
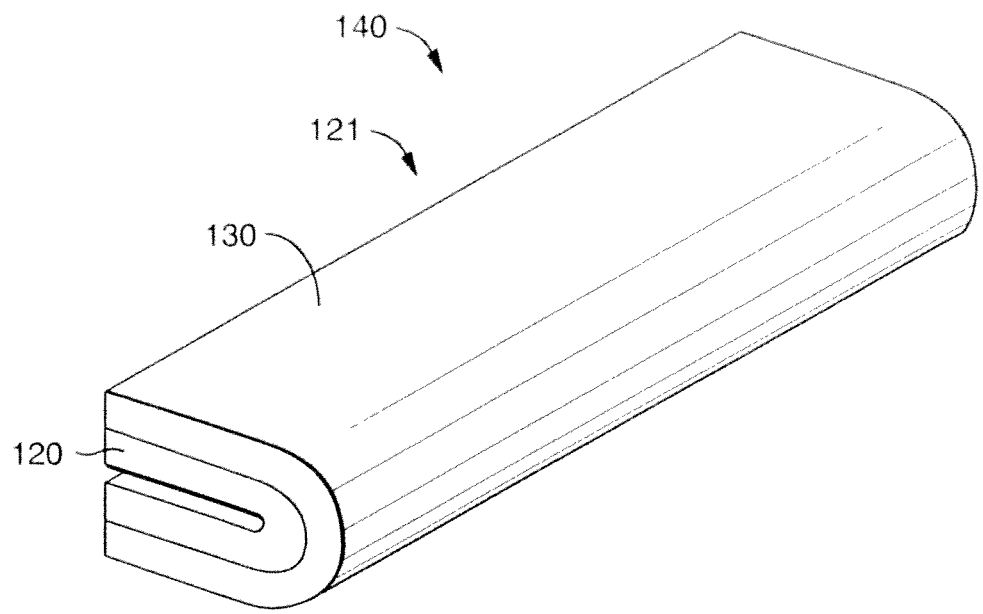
FIG. 10A is a perspective view of a starting structure after being folded along its longitudinal central axis to form a tubular elongated member.
Figure 10B:
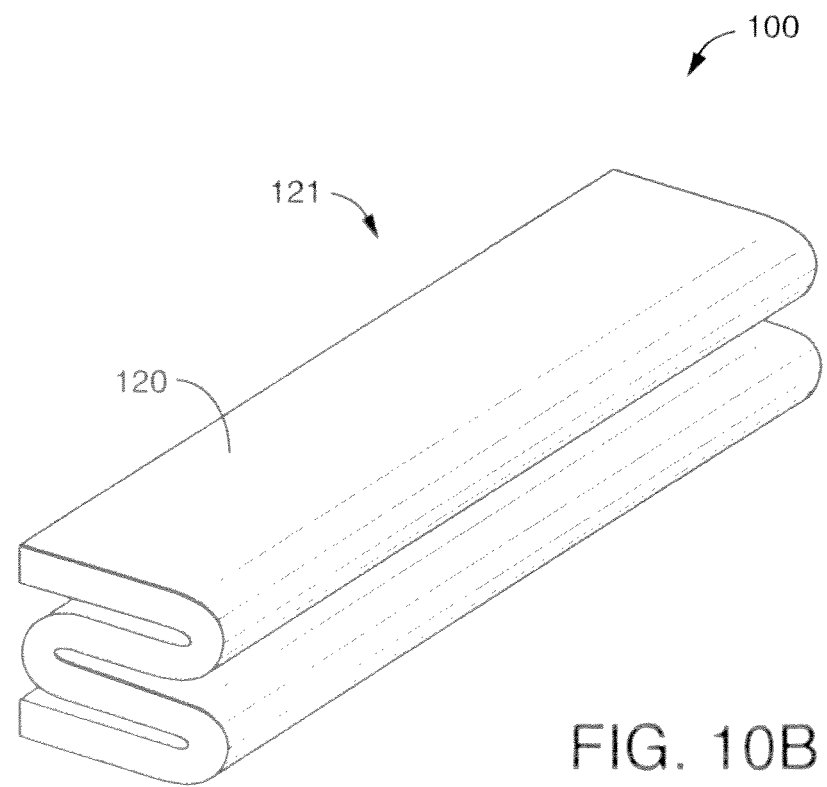
FIG. 10B is a perspective view of a starting structure after being folded along multiple longitudinal axes into a fan folded configuration to form a tubular elongated member.
Figure 11A:
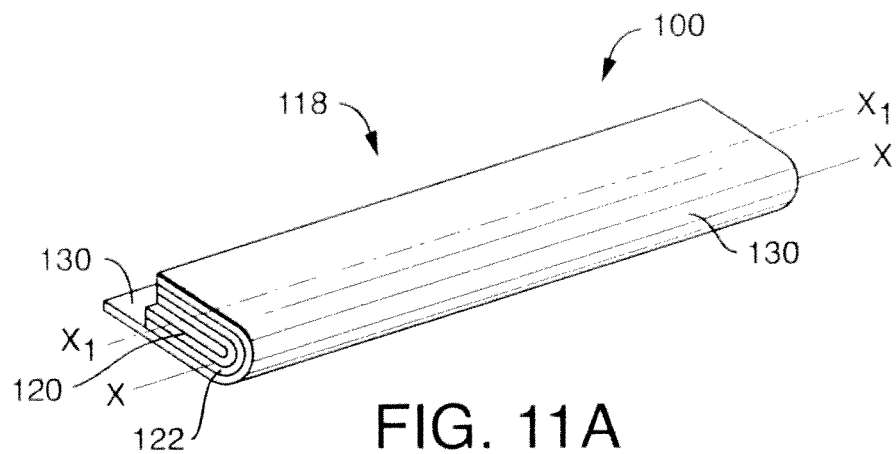
FIG. 11A is a perspective view of a starting structure after being folded along its longitudinal central axis.
Figure 11B:
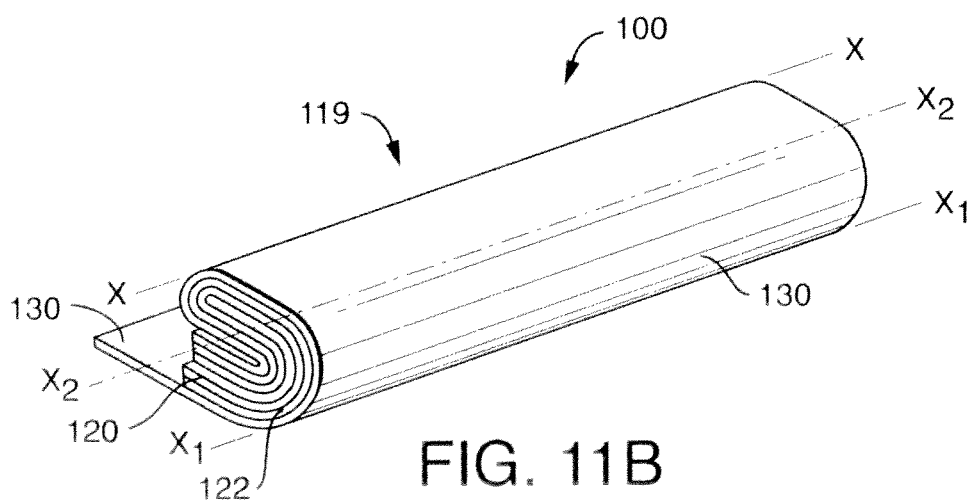
FIG. 11B is a perspective view of the starting structure of FIG. 11A after being folded a second time along its new longitudinal central axis.
Figure 11C:
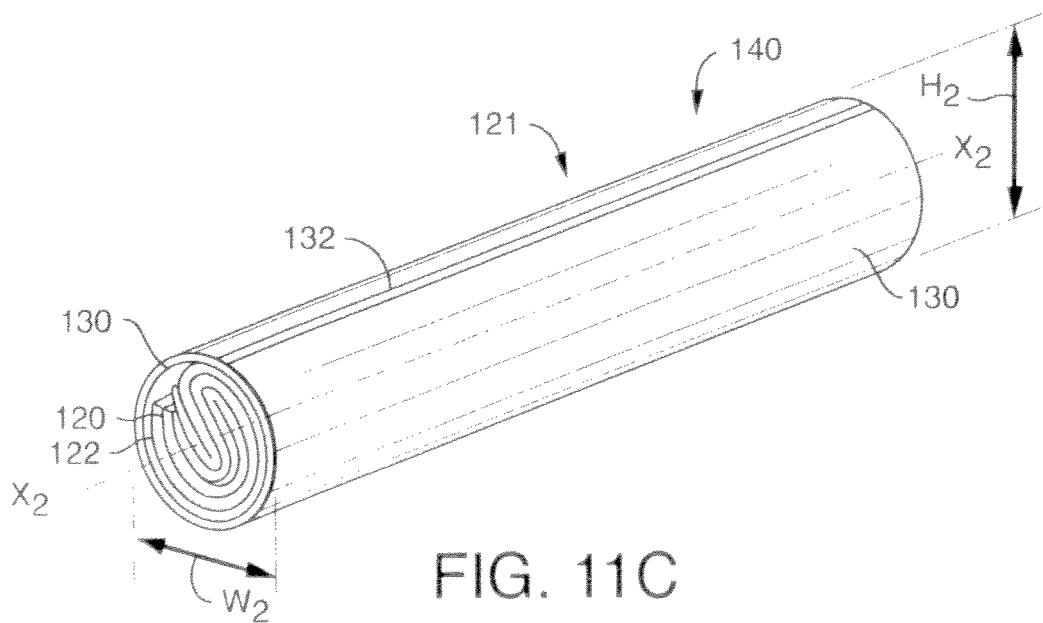
FIG. 11C is a perspective view of the starting structure of FIG. 11B after being rolled to form a tubular elongated member.

In some aspects, the starting structure 100 is formed into an elongated member in the form of a softwind before shaping into a disposable urinary incontinence device 110 of the present invention. This can be accomplished by folding, rolling, and/or radially compressing the starting structure 100. For example, FIG. 10A illustrates a starting structure 100 that has been folded along its central longitudinal axis to form the elongated member 140. In another example, FIG. 10B illustrates a starting structure 100 that has been folded along multiple longitudinal axes to form the elongated member 140. In still another example, FIGS. 11A-11C illustrate a rolled elongated member 140. FIG. 11A illustrates a starting structure 100 comprising a resilient member 120, an additional layer 122 and a cover sheet 130 that is first folded along the central longitudinal axis X-X to obtain a first folded member 118 having a new central longitudinal axis $X_1$-$X_1$. FIG. 11B illustrates that the first folded member 118 of FIG. 11A is then folded a second time along central longitudinal axis $X_1$-$X_1$ to obtain a second folded member 119, having a new central longitudinal axis $X_2$-$X_2$. FIG. 13 illustrates that the free end of the cover sheet 130 the second folded member 119 of FIG. 11B is then be rolled over upon itself and is bonded or attached, or left unattached if desired, to form the elongated member 140.

In some aspects, the longitudinal end portions 135 of the cover sheet 130 of the elongated member 140 can be sealed to form end seals 134, such as shown in FIG. 12. FIG. 12 illustrates an elongated member 140 comprising a resilient member 120 enveloped by a cover sheet 130. In the illustrated embodiment, the cover sheet 130 has a greater length $L_3$ than the resilient member 220 length $L_1$, although it need not be. The longitudinal end portions 135 are then bonded to form the end seals 134 using bonding means well-known in the art, such as heat, pressure, ultrasonic, stitching, adhesives and the like. In embodiments where $L_3$ is greater than $L_1$, the end seals 134 can be partially or completely devoid of resilient member 120 material.

In some aspects, the elongated member 120 can have compression properties. For example, the elongated member can have an Energy Loading from 20 $g_f$ to 80 $g_f$, an Energy UnLoading from 20 $g_f$ to 50 $g_f$ and a Hysteresis Loss from 40% to 50%.

The elongated member 140 can be folded to form a disposable urinary incontinence device 110 of the present invention. In desirable aspects, the urinary incontinence device 110 of the invention has a "W-shaped" profile, such as shown in FIG. 1. With reference to FIGS. 13A-D, to form a "W-shaped" urinary incontinence device 110, the elongated member 140 is first folded or bent upon itself longitudinally 1 at fold region 112 located at the approximate longitudinal 1 center of the elongated member 140 such that, in the case of the illustrated embodiment, the first end 162A and 164A are transversely aligned, and the first end portion 162 and the second end portion 164 are longitudinally 1 aligned adjacent to one another to form elongated portions 191 and 192, as defined by dashed line 170. By being aligned "adjacent to one another" it is meant that the first end portion 162 and the second end portion 164 are positioned side by side, parallel to one another, or offset axially, or spaced transversely 2 apart from one another, or are positioned in some type of arrangement whereby the first end portion 162 and the second end portion 164 are transversely 2 close to one another. However, it is not critical that fold region 112 is located at the longitudinal 2 center of the elongated member 140, or that the first end 164A and the second end 162B are transversely aligned. For example, in some aspects, the fold region 112 can be located a desired distance from the longitudinal 1 center of the elongated member 140, such that the first end 162A and the second end 164A are staggered (i.e., not transversely 2 aligned). In addition, in aspects where the device 110 comprises a cover sheet 130, the longitudinal bond 132 (or folded edge) of the cover sheet 130 can be positioned to the inside (i.e., face away from the skin) when the elongated member 140 is folded at fold region 112.

In some desirable aspects, elongated portions 191 and 192 can be apertured to form a first opening (aperture) 54A and a second aperture 54B, respectively, which extend partially or completely through elongated portion 191 and elongated portion 192, such as shown in FIG. 13B. The apertures 54A,54B can be formed transversely 2 perpendicular to the longitudinal axis 1, or at an angle thereto. Preferably, the apertures 54A,54B are spaced a short distance from the first end 162A and the second end 164A, such as about 2 mm to about 20 mm, such as about 4 mm to about 15 mm, or about 5 mm to about 10 mm from each end 162A,164A. In aspects where the ends 162A,164A are staggard, the distance of aperture 54A from end 162A can be different than the distance of aperture 54B from end 164A. The apertures 54A,54B are designed to allow a withdrawal member 56 to be looped therethrough to assist in removing the disposable urinary incontinence device 110 from a woman's vagina, and to help secure the alignment of the end portions 162,164; thus, in some desirable aspects, the apertures 54A,54B are substantially transversely 2 aligned. The apertures 54A,54B can be formed with a needle, an awl or other suitable piercing means well-known to those skilled in the art. In the illustrated embodiment, the withdrawal member 56 can be threaded through both apertures 54A,54B and then looped upon itself so as to cinch the withdrawal member 56 securely to the elongated member 140.

In some aspects, the free ends 56A and 56B of the withdrawal member 56 can then be tied into a knot 58 to assure that the withdrawal member 56 will not separate from the device 110. The knot 58 can also serve to prevent fraying of the withdrawal member 56 and can provide a place or point where a woman can grasp the withdrawal member 56 when she is ready to remove the disposable urinary incontinence device 10 from her vagina.

In the illustrated embodiment, it should be noted that the withdrawal member 56 also holds the end portions 162A, 164A in direct contact with one another and can limit the amount that the device 110 will expand (i.e., unfold) while positioned within the woman's vagina. In some aspects, the apertures 54A,54B can alternatively be formed in the elongated member 140 before it is folded, and the withdrawal member 56 can be attached either before or after the elongated member 140 is folded.

The withdrawal member 56 can be constructed from various types of strings, threads or ribbons that are well known in the art, such as cotton, nylon, polypropylene and the like. The withdrawal member 56 should have a length which extends beyond the withdrawal end 52 of the W-shaped urinary incontinence device 110 of from about 50 mm to about 200 mm, such as from about 75 mm to 150 mm, or from about 100 mm to about 130 mm. The withdrawal member 56 can be dyed and/or treated with an anti-wicking agent, such as wax, before being secured to its respective pledget. The anti-wicking agent can reduce and desirably prevent vaginal fluids from wicking along the withdrawal member 56 and contacting the inner surface of a woman's undergarment.

Figure 2:
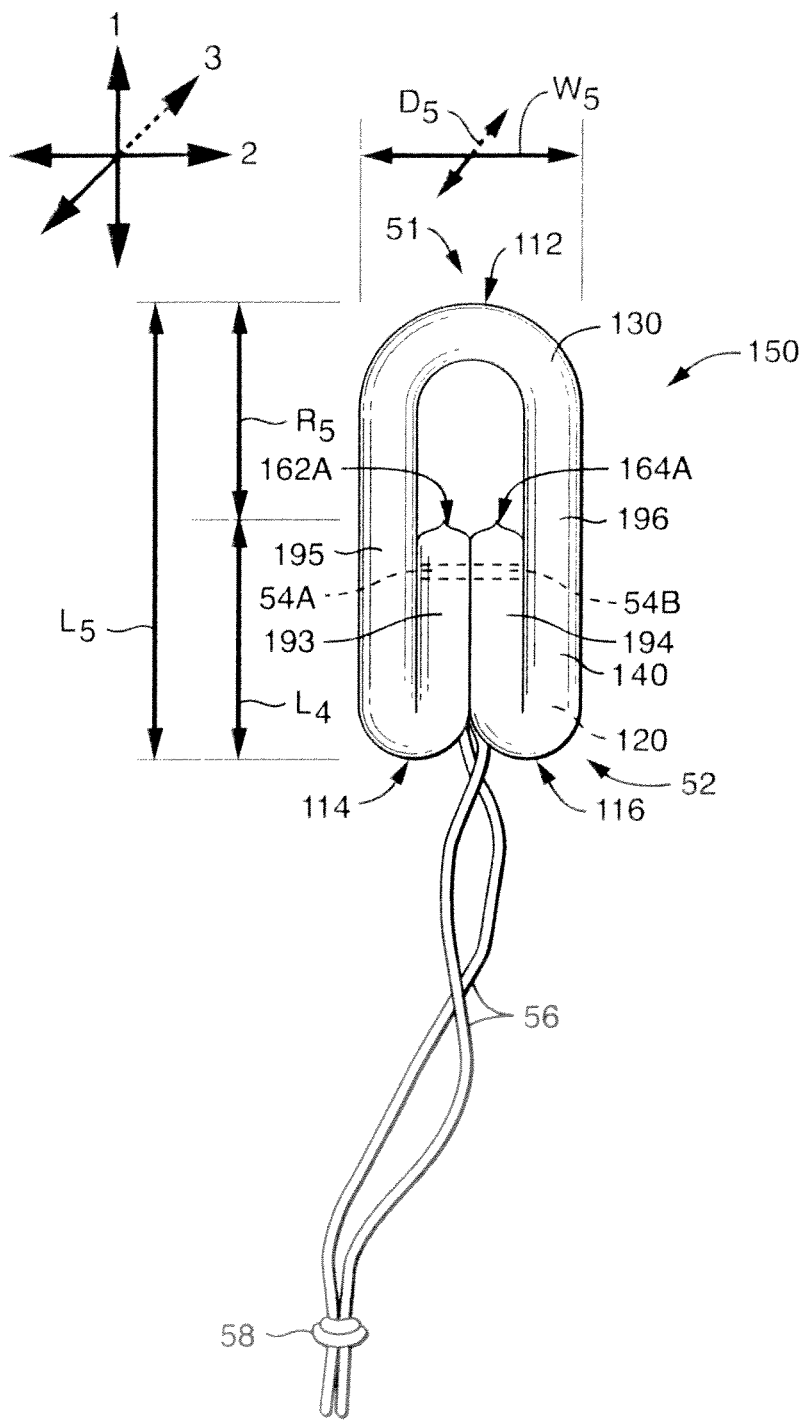
FIG. 2 is a side view of a disposable urinary incontinence device after it has been compressed into a pledget.

In desirable aspects, the elongated member 140 is folded a second time between the first end 162A and fold region 112 to form fold region 114, and the elongated member 130 is folded a third time between the second end 164A and fold region 112 to form fold region 116. Thus, the disposable urinary incontinence device 110 of the present invention will have three fold regions 112,114,116 which are located between the first and second ends 162A,162B of the elongated member 140, providing a first portion 193 (defined by end 162A and line 171), a second portion 194 (defined by end 164A and line 172), a third portion 195 (defined by line 171 and line 170) and a fourth portion 196 (defined by line 172 and line 170), such as shown in FIG. 13C, to form the generally W-shaped profile of the device 110. In the generally W-shaped profile of the illustrated embodiment, the first and second ends 162A and 164A are transversely 2 aligned substantially adjacent to one another, the first portion 193 and the second portion 194 are aligned substantially adjacent to one another, the first portion 193 and the third portion 195 are aligned substantially adjacent to one another, the second portion 194 and the fourth portion 196 are aligned substantially adjacent to one another, and the first portion 193 and the second portion 194 are disposed between the third portion 195 and the fourth portion 196. In some aspects, the first portion 193 and the second portion 194 desirably have approximately the same length, although their lengths can differ if desired, and the third portion 195 and the fourth portion 196 desirably have approximately the same length, although their lengths can differ as well if desired. In the illustrated embodiment, the first portion 193 and the second portion 194 have a length $L_4$ that is less than the length $L_5$ of the third portion 195 and the fourth portion 196, such as shown in FIG. 2. By way of example only, if the third portion 195 and the fourth portion 196 have a length $L_5$ of 50 mm, then the first portion 193 and the second portion 194 can each have a length of 30 mm, such as 20 mm, for instance.

As referenced above, the fold region 112 can be positioned an equal or an unequal distance between the first and second ends 162A, 164A of the elongated member 140. When the fold region 112 is positioned an equal distance between the first and second ends 162A, 164A, such as in the illustrated embodiment of FIG. 13C, the fold region 112 will be axially aligned along a central longitudinal axis Z-Z of the device 110 (also referred to as the "longitudinal 1 center" of the elongation member 140). In this example, the central longitudinal axis Z-Z vertically divides the generally W-shaped profile of the device 110 into left and right mirror images.

In some aspects, particularly those that comprise a cover sheet 130, an embossment can be applied to the cover sheet 130 of the elongated member 140 at the point of each desired fold region to provide fold guides 550. The fold guides 550 encourage the elongated member 140 to be folded at predetermined points. Typically, the embossed fold guide 550 will accordingly have a higher density and stiffness than the remainder of the cover sheet 130; thus, the fold regions will often occur adjacent to the fold guides 550, rather than directly on the fold guides 550. In some aspects, the fold guides 550 are located on the skin-facing side of the pledget (although they need not be); thus, the fold guides 550 can desirably be gentle to the skin. The embossment of the fold guides 550 can have any desirable emboss pattern, such as slanted parallel lines or diamonds for example, and the emboss pattern can also be visually appealing.

The disposable urinary incontinence device 110 having a W-shaped profile of the illustrated example can have a Transverse Device Compression which is the compression force of the device 110 in the transverse 2 direction (i.e., the force exhibited as the device tends toward unfolding when being compressed), such as shown in FIG. 18. In some aspects, the device 110 can have a Transverse Device Compression from 100 $g_f$ to 900 $g_f$, such as between 200 $g_f$ and 400 $g_f$. For example, a device 110 with a W-shape consisting of an tubular-shaped elongated member 120 having a diameter 20 mm and a length of 175 mm comprising a resilient member consisting of Texor Surge 5.25 having a width of 13 mm, a length of 17 mm and a basis weight of 150 gsm disposed within a CDR-421034 Perforated Film cover sheet exhibited a Transverse Device Compression of 353 $g_f$, as measured by the Transverse Device Compression Test. In another example, a device 110 with a W-shape consisting of an tubular-shaped elongated member 120 having a diameter 20 mm and a length of 175 mm comprising a resilient member consisting of Texor Surge 5.25 having a width of 13 mm, a length of 17 mm and a basis weight of 150 gsm disposed within an EX-1824027 cover sheet exhibited a Transverse Device Compression of 224 $g_f$, as measured by the Transverse Device Compression Test.

Referring to FIG. 13D, the W-shaped disposable urinary incontinence device 110 is then compressed into a pledget 150 having an insertion end 51 and a trailing end 52. The pledget 150 can have any desired overall compressed shape, but in desirable aspects, it will have a generally cylindrical shape with a circular or oval cross-sectional configuration, taking on the shape of an applicator, for example. An alternative profile would be a rectangular or triangular cross-sectional configuration, although other profiles are also contemplated.

In general, the pledget 150 has an overall longitudinal 1 length $L_5$, an overall transverse 2 width $W_5$ and a depth $D_5$ which runs along the z-axis 3, such as shown in FIG. 2. When the pledget 150 is round in cross-section, its width $W_5$ will be equal to its depth $D_5$, and when the pledget 150 is elliptical in cross-section for instance, its width $W_5$ will be greater than its depth $D_5$. The length $L_5$ of the pledget 150 can range from about 30 mm to about 120 mm, such as from about 40 mm to about 100 mm, or about 50 mm to about 70 mm. The width $W_5$ and depth $D_5$ can range from about 10 mm to about 50 mm, such as from about 20 mm to about 40 mm, or from about 25 mm to about 35 mm.

The pledget 150 also has a dimension $R_5$ which is the distance between the apex of fold region 112 and the closest end 162A, 164A of the elongation member 140. In the illustrated embodiment, the dimension $R_5$ is equal in distance to between the apex of fold region 112 and the both ends 162A, 164A, although it need not be. The dimension $R_5$ can range from about 10 mm to about 100 mm, such as from about 20 mm to about 80 mm, or from about 35 mm to about 50 mm. Another way of stating the length of the dimension $R_5$ is to say that it should have a distance which is equal to at least about 10-percent, such as at least about 25-percent, of the length $L_5$ of the pledget 150. The distance $R_5$ should desirably be sufficient to ensure that the pledget 150 has a less dense and more comfortable insertion end, and yet can laterally expand outward at the trailing end 52 to provide pressure against the interior walls of the vagina.

Figure 14A:
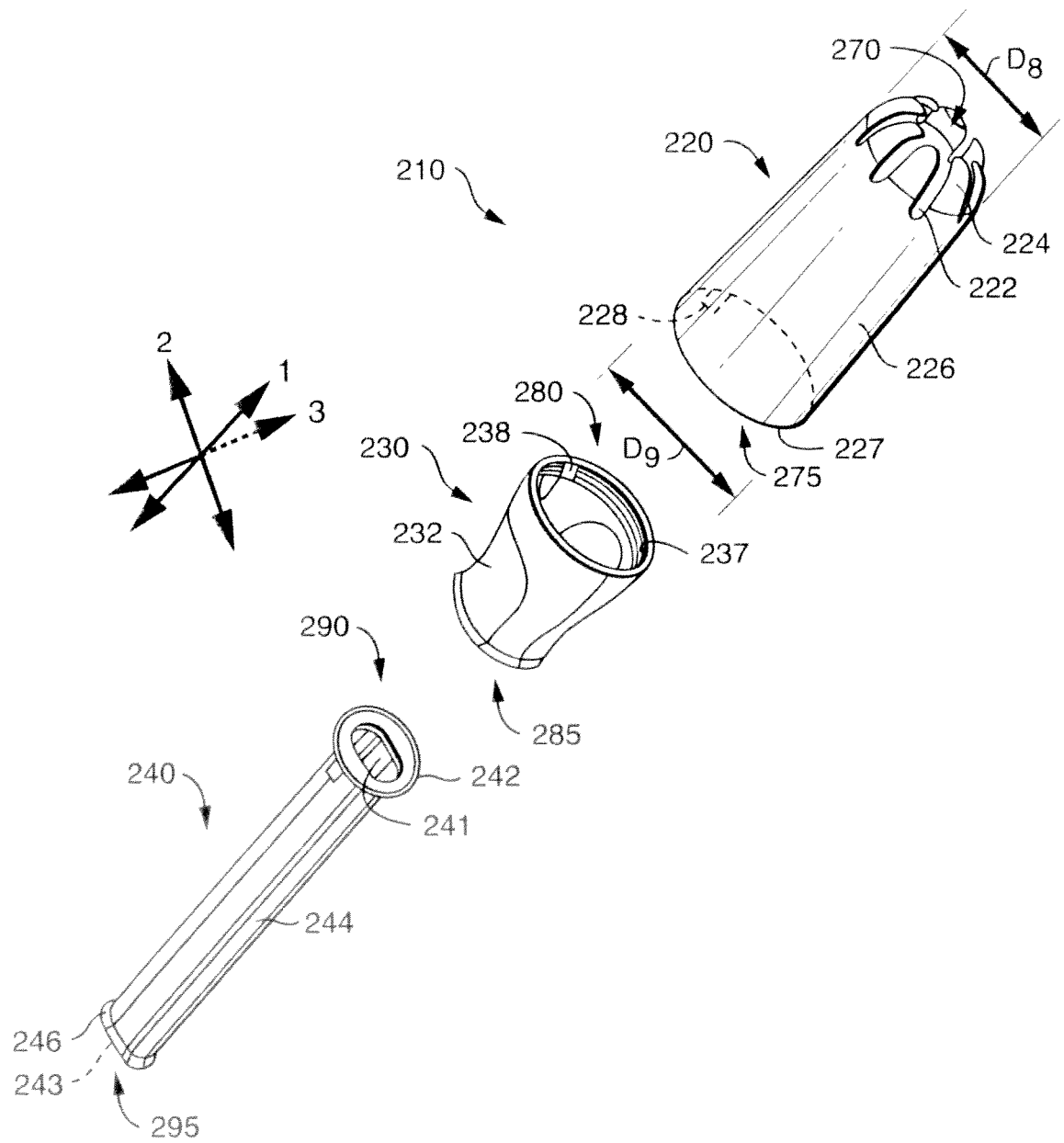
FIG. 14A is a perspective view of an exemplary applicator in a pre-assembled condition.

The insertion end 51 of the pledget 150 is designed to be the first end of the pledget 150 that enters into the woman's vaginal cavity during insertion. It should be noted that, while in use, the pledget 150 will be entirely positioned within the woman's vagina, such as seen in FIGS. 3 and 4. The insertion end 51 will generally contain a lesser amount of overall material than the trailing end 52 of the pledget 150. In some aspects, even though a lesser overall amount of material may be present at the insertion end 51, the outside diameter of the insertion end 51 can be equal to the outside diameter of the trailing end 52 when in a compressed state, such as when the pledget 150 is disposed within an applicator. To achieve this, the amount of overall material in the insertion end 51 will be densified or compressed to a lesser extent than the overall material making up the trailing end 52. By having a greater amount of material present at the trailing end 52, the urinary incontinence device 110 is better suited to expand at the trailing end and support the musculature and the body tissue located adjacent to the urethra and facilitate urethral compression to at least partially or completely eliminate the involuntary escape of urine through the urethra. Of course it is understood that if the compressed pledget 150 is disposed into a tapered applicator, such as seen in FIGS. 14A, 14B and 14C, the diameter of the insertion end 51 of the compressed pledget 150 would be less than the diameter of the trailing end 52. In other words, the shape of the compressed pledget will at least be partially determined by the interior shape of the applicator, if present.

The use of the device 110 is illustrated in FIGS. 3 and 4. FIG. 3 illustrates the device 110 in a position which is adjacent to the sphincter muscle 84. FIG. 4 illustrates that the device 110 in a position that is lower in the vaginal cavity than in FIG. 3, up to the vaginal opening 91.

In FIGS. 3-4, the compressed pledget 150 is depicted having been inserted into a woman's vagina 92 and the pledget 150 is shown in an expanded state 40'. The expanded pledget has a length $L_6$ and a diameter or width $W_6$. The first and second end portions 162,164 desirably remain adjacent to, and in contact with, each other by the attachment of the withdrawal member 56. While within the vaginal cavity 92, the liquid-stable resilient member 120 will expand (both radial expansion and unfolding expansion) thereby causing the W-shaped device 110 to spring or expand outward and/or upward and spread across a portion of the internal vaginal space. Desirably, the device 110 should be positioned below the cervix. The resilient, elastic and flexible characteristics of the resilient member 120 enables the device 110 to recover quickly from its compressed and deformed pledget 150 shape. This allows the urinary incontinence device 110 to intimately contact and conform more ideally to the space within the vaginal walls and press against the inside anterior and posterior and right and left lateral walls and convolutions of the vagina 92.

An additional aspect of this invention comprises a means of adjusting the width dimension $W_6$ of the device 110 to increase the pressure against the vaginal walls, if necessary, by pulling on the withdrawal member 56 while an applicator 210 (FIGS. 14A-C) remains within the vagina and when the insertion end 270 is adjacent to, and in contact with, the trailing end 52 of the urinary incontinence device 10 after the device 110 has been ejected from the applicator 210. The presence of the applicator 210 will prevent the device 110 from being removed during adjustment and will draw first and second portions 193,194 of urinary incontinence device 110 downward, thus increasing the $R_5$ dimension (FIG. 2) and the $W_6$ dimension (FIGS. 3 and 4).

Another aspect of this invention comprises a means of adjusting the width dimension $W_6$ (FIGS. 3 and 4) to decrease the pressure against the vaginal walls for removal. This can be accomplished by pulling on the withdrawal member 56 while an applicator 210 (FIGS. 14A-C) remains within the vagina and when the insertion end 270 is adjacent to, and in contact with, the trailing end 52 of the urinary incontinence device 10 after the device 110 has been ejected from the applicator 210 until the device 110 resembles the shape profile shown in FIG. 13B. This configuration minimizes the width dimension $W_6$, thus decreasing the pressure on the vaginal walls, and making removal more comfortable.

Comparing the compressed pledget 150 shown in FIG. 2 to the expanded device 110' shown in FIGS. 3 and 4, the width $W_6$ of the trailing end 52' of the inserted device 110' is greater than the width $W_5$ of the trailing end 52 of the compressed pledget 150. In addition, the distance $W_7$ of the expanded insertion end 51' of the inserted device 110' can be greater than distance $W_5$ of the insertion end 51 of the compressed pledget 150. Furthermore, the length $L_6$ of the inserted device 110' can be equal to or slightly larger than the length $L_5$ of the compressed pledget 150. In addition, the diameter $D_6$ of the inserted device 110' can be equal to or slightly larger than the diameter $D_5$ of the compressed pledget 150. Accordingly, the dimensions $L_5$, $W_5$ and $D_5$ of the compressed pledget 150 can each increase once the compressed pledget 150 is inserted into the vagina 92 due to the expansion of the resilient member 120. As the pledget 150 expands by the action of the resilient member 120 to its respective expanded state 40', the expanded pledget will allow for pressure transmission across body tissue and in particular, in the urethro-vaginal myofascial area 86. This action can provide a stable backdrop to allow the woman's urethra 88 to become compressed upon itself when intra-abdominal pressure increases. For example, a part of the urethra 88 which is about 1.5 inches (38 mm) long and through which urine flows, will be compressed or pinched upon itself thereby preventing the urine from passing through. In addition, support will be provided to the region near the sphincter muscle 84 so that it has a higher tendency to maintain a circular cross-sectional configuration and operate properly. One or both of these actions will reduce and/or prevent involuntary urine loss due to stress urinary incontinence.

The compressed pledget 150 can be housed in a nonwoven, cardboard, polymeric (e.g., plastic) and the like applicator to facilitate insertion of the urinary incontinence device 110 into a woman's vagina 92. In general, the applicator can be constructed of one or more hollow tubes which can retain the device 110 in the form of a compressed pledget 150 at a set length, width and/or diameter. Furthermore, insertion of the pledget 150 from the applicator into the human body can be accomplished by using a plunger 240, such as in a two-piece or three-piece applicator, or by digital insertion, whereby the user can use one of her fingers to insert the device 110 rather than an applicator. Suitable applicators are disclosed in U.S. Pat. No. 6,645,136 to Zunker et al., which is incorporated herein by reference in a manner that is consistent herewith.

For exemplary purposes only, FIGS. 14A, 14B and 14C show a suitable applicator. With reference to FIG. 14A, an applicator 210 is shown in a pre-assembled configuration. The applicator 210 includes a barrel portion 220 defining an insert carriage or insert housing having slits or openings 222 defining individual petals 224 at the insertion end 270 of the barrel portion 220; a gripping portion 230 that attaches to the trailing end 275 of the barrel portion 220; and a plunger portion 240 that fits through the opening at the trailing end 285 of the gripping portion 230 for discharging the pledget 150 from the barrel 220.

The barrel 220 includes a hollow cylinder 226 extending substantially parallel to a longitudinal axis 1 adapted to house and carry the compressed pledget 150 therein. In a direction substantially perpendicular to its longitudinal axis 1, the barrel 220 of the illustrated embodiment has a substantially oval or elliptical cross-section (although it need not be) defining a major axis 2 and a minor axis 3. The barrel 220 has a urinary incontinence device discharging exit end (i.e., insertion end) 270 and a trailing end 275. The insertion end 270 is the leading, vaginal insertion end when the applicator 210 is inserted into the vagina 92. The insertion end portion 270 of the cylinder 226 preferably includes flanges defining petals 224, which soften the vaginal insertion process. Accordingly, the petals 224 are desirably flexible, enabling the pledget 150 to be ejected therethrough when the plunger 240 is pressed against the trailing end 52 of the pledget 150 within the barrel 220. The illustrated embodiment comprises eight petals 224; however, any number of petals can be suitable, such as 1-10 petals, for example. Alternatively, in some aspects, the insertion end portion 270 may have 0 petals.

In some aspects, the barrel 220 can be tapered such that the insertion end 270 has a smaller cross-section diameter $D_8$ than the trailing end 240 diameter $D_9$, although it need not be. An exemplary tapered barrel can be seen in FIGS. 14B and 14C by comparing the longitudinal edge 229' of the barrel portion 220 to vertical line 229. Such a design may be desirable for easier insertion of the applicator 210 into the vaginal cavity. Such a design may also be desirable in some aspects when fitting the compressed pledget 150 into the barrel portion 220 since the trailing end 52 of the pledget 150 comprises more material than the insertion end 51.

The insertion end 280 of the gripping portion 230 attaches to the trailing end 275 of the barrel 220. In some aspects, the gripping portion 230 can include a mechanical snap 237 at the insertion end 280 that joins to a mating snap 227 at the trailing end 275 of the barrel 220 so that the barrel 220 and gripping portion 230 do not separate during use. In some additional aspects, the gripping portion 230 can include a slot 238 that can mate with a complementary tab 228 located on the trailing end 275 of the barrel 220 to prevent the barrel 220 and gripping portion 230 from turning relative to each other.

In some aspects, the trailing end 285 of the gripping portion 230 has a decreased or tapered width or diameter relative to the insertion end 280 of the gripping portion 230, which serves as a guide and/or an insertion stop for the plunger 240 at the head flange 242 when the plunger 240 is extended and/or at the rear flange 246 when the plunger 230 is depressed. In some aspects, the trailing end 285 of the gripping portion 230 can have one or more substantially flattened surfaces as compared to the insertion end 280 which can help hold and guide the plunger 240, and/or provide a surface for the user's fingers. Accordingly, in some aspects, the general cross-sectional configuration of the trailing end 285 of the gripping portion 230 is desirably similar or comparable to that of the shaft 244 of the plunger 240 to accommodate smooth axial engagement between the gripping portion 230 and the plunger 240. In some aspects, the gripping portion 230 can include a plurality of engaging portions 236 defined by extensions within the interior portion of the gripping portion 230 for contacting the exterior of the plunger 240 adapted to secure the plunger 240 in place and/or for guiding it during insertion or withdrawal of the applicator 210.

In some aspects, the gripping portion 230 can include a finger contour 232 designed to more comfortably fit the user's fingers. The finger contour 232 can assist the user when holding or inserting the applicator 210, and in some aspects, can assist the user with proper orientation of the applicator 210. In some further aspects, such as seen in FIGS. 14B and 14C, a grip layer 234 can be attached to the finger contour 232 to provide additional benefits, such as improved frictional gripping and/or a softer and more comfortable feel, for example. Thus, the grip layer 234 can be made out of any desired material, such as a thermoplastic elastomer, for example.

The plunger portion 240 of the applicator 210 in the illustrated embodiment includes a head flange portion 242, a shaft portion 244 and a rear flange portion 246. Like the trailing end 285 of the gripping portion 230, the plunger 240 can have a substantially rectangular or race-track (i.e. two flat sides and two curved sides) cross-section profile having a major axis 2 and a minor axis 3 in a direction perpendicular to its longitudinal axis 1. In some aspects, the corners and/or sides of the plunger 240 can have some radius of curvature, which can reduce frictional contact of the plunger 240 with the inner surfaces of the gripping portion 230, and can enhance the aesthetic appearance of the applicator 210. The plunger 240 is desirably hollow, and has exits 241 and 243 for threading the withdrawal member 56 through the interior of the plunger 240 and out the trailing end 295 of the plunger 240. The head flange portion 242 and rear flange portion 246 can be integrally formed with the shaft portion 244. The head flange portion 242 is located at the insertion end 290 of the plunger and can have a larger cross-section dimension than the shaft portion 244, such that it can more easily push the pledget 150 out of the barrel 220. The rear flange portion 246 is located at the trailing end 295 of the plunger 240 and can have a slightly larger cross-section dimension than the shaft portion, such that a user's finger can more easily engage the plunger 240 during insertion. In some aspects, the plunger 240 can be reinforced by support members integrally formed within the interior and/or on the exterior of the plunger 240.

The invention also includes a method of forming an elongation member 130 with an a longitudinal exterior seam 132. With reference to FIGS. 15A and 15B, an exemplary method of forming the elongation member can include the followings steps:

Step 1) A web of liquid-stable resilient member material 120' is provided having a desired width and thickness.

Step 2) Optionally (not shown), one or more additional layers may be aligned on either surface of the resilient member 120.

Step 3) The resilient member material 120' is formed into a tubular shape, such as by drawing it through a radially constricting device 318 resulting in a randomly folded tubular-shaped resilient member 120. A transverse cross-section view of member 120 is shown in FIG. 15B.

Step 4) The resilient member 120 can be optionally embossed to form fold regions. Locating the embossments 113 interior to the lateral edge of the resilient member 120 can reduce the possibility of irritation to the user of the end product.

Step 5) A cover sheet material 130' is provided.

Step 6) The resilient member 120 enters tube opening 320 and is drawn into tube 319 by applying a longitudinal 1 tension.

Step 7) The cover sheet material 130' is wrapped around tube 319.

Step 8) The lateral ends of the material 130' are attached using heat and pressure to form a cover sheet 130 having a longitudinal seam 132.

Step 9) The resilient member 120 and the cover sheet 130 exit tube 319 at opening 321. Desirably, tube opening 321 has a smaller diameter than tube opening 320.

Step 10) The resilient member 120 expands radially and fills the sealed cover sheet 130 forming a continuous elongation member 140'.

Step 11) The continuous elongation member 140' is segmented (i.e., cut) into individual elongation members 140. Releasing the tension on the resilient member 120 by cutting the continuous elongation member 140' results in a longitudinal 1 length reduction of the resilient member 120, resulting in an elongated member 140 that is devoid of resilient materials at the longitudinal ends 135.

Step 12) The longitudinal ends 135 of the elongation member 140 are sealed using heat and pressure to form end seals 134.

Figure 16:
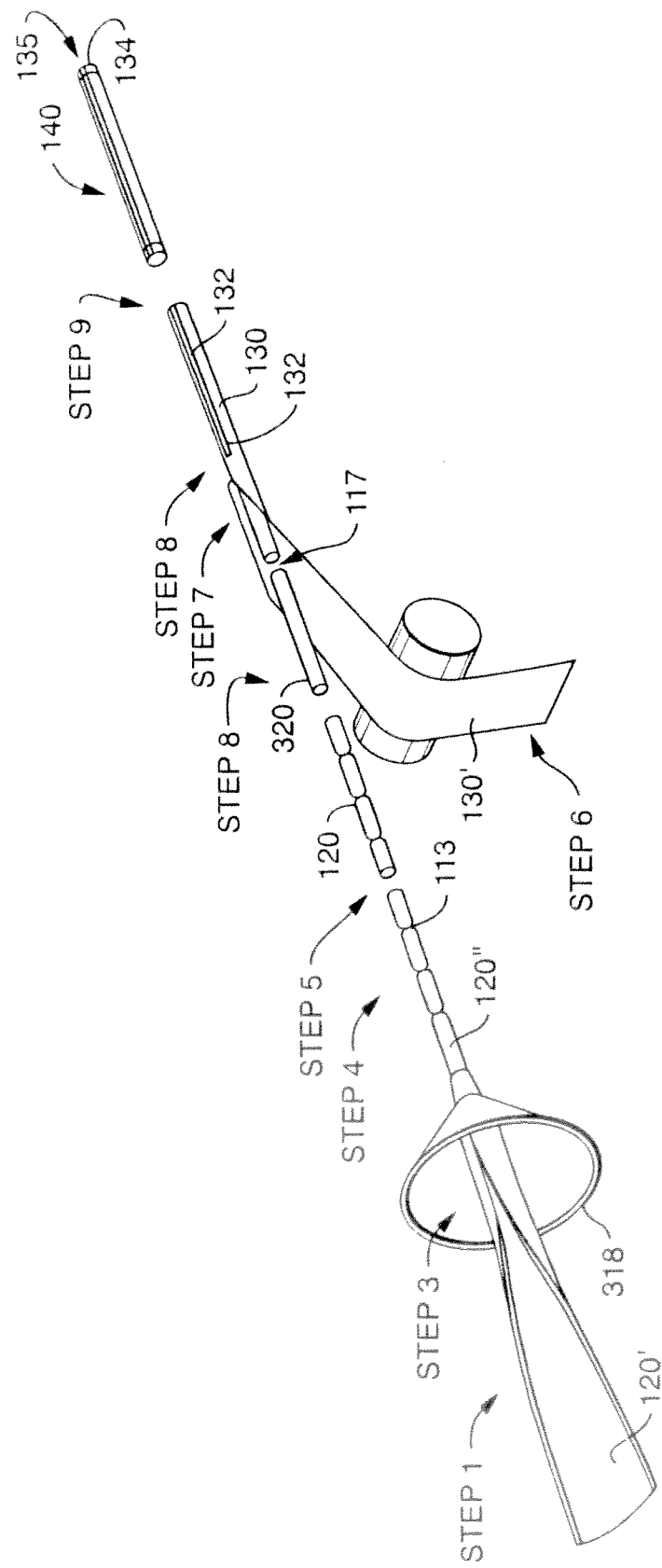
FIG. 16 is a perspective view of a method of making an elongation member of the present invention.

With reference to FIG. 16, another exemplary method of forming an elongated member 140 is presented. The method can include the followings steps:

Step 1) A web of liquid-stable resilient member material 120' is provided having a desired width and thickness.

Step 2) Optionally (not shown), one or more additional layers may be aligned on either surface of the resilient member 120.

Step 3) The resilient member material 120' is formed into a tubular shape, such as by drawing it through a radially constricting device 318 resulting in a continuous randomly folded tubular-shaped resilient member 120".

Step 4) The continuous resilient member 120″ can be optionally embossed to form fold regions. Locating the embossments 113 interior to the lateral edge of the resilient member 120 can reduce the possibility of irritation to the user of the end product.

Step 5) The continuous resilient member 120″ is segmented (i.e., cut) into individual resilient members 120.

Step 6) A cover sheet material 130′ is provided.

Step 7) The cover sheet material 130′ is wrapped snuggly around the individual resilient members 120. A gap 117 of predetermined length is maintained between successive resilient members 120.

Step 8) The lateral ends the cover sheet material 130′ are attached forming seam 132 resulting in a tubular-shaped cover sheet 130.

Step 9) The cover sheet 130 comprising individual resilient members 120 is sealed by heat and pressure at the location of the gap 117, and then segmented to form an elongated member 140 having longitudinal end seals 134.

The invention also provides a method for alleviating female urinary incontinence. The method comprises the steps of:

a) providing the disposable urinary incontinence device 110 of the present invention comprising a liquid-stable resilient member 120 and a cover sheet 130 that envelops the liquid-stable resilient member 120 to form an elongated member 140 having a tubular profile, wherein the elongated member 140 has a first end 162A, a second end 164A, a first fold region 112 disposed between the first end 162A and the second end 164A, a second fold region 114 disposed between the first end 162A and the first fold region 112, a third fold region 116 disposed between the second end 164A and the first fold region 112;

b) folding the elongated member 140 at the first fold region 112, the second fold region 114 and the third fold region 116 to form a first portion 193 located between the first end 162A and the second fold region 114, a second portion 194 located between the second end 164A and the third fold region 116, a third portion 195 located between the first fold region 112 and a second fold region 114, and a fourth portion 196 located between the first fold region 112 and the third fold region 116 to provide an elongated member 140 is in a folded condition, wherein the first portion 193 is substantially aligned adjacent to the second portion 194, the first portion 193 is substantially aligned adjacent to the third portion 195, the second portion 194 is substantially aligned adjacent to the fourth portion 196, and the first portion 193 and the second portion 194 are disposed between and substantially adjacent to the third portion 195 and the fourth portion 196 to form a disposable urinary incontinence device 110 having a W-shaped profile;

c) compressing the disposable urinary incontinence device 110 having a W-shaped profile into a compressed pledget 150 having an insertion end 51 and a trailing end 52;

d) inserting the compressed pledget 150 into a woman's vagina 92 with the insertion end 51 entering first;

e) positioning the compressed pledget 150 within the vaginal cavity 92 at a location ranging from the urethral sphincter muscle 84 to the vaginal opening 91;

f) allowing the compressed pledget 150 to expand within the vaginal canal 92 to form an inserted disposable urinary incontinence device 110′ to provide pressure to the urethrovaginal myofascial area 86; and e) permitting the urethra 88 to be compressed upon itself thereby limiting involuntary urine flow.

In some aspects, the method further comprises attaching a withdrawal member 56 to the first portion 193 and the second portion 194 of the elongated member. In some aspects, the method further comprises inserting the compressed pledget 150 into an applicator 210. In some aspects, the method further comprises, gripping the applicator 210 at the gripping portion 230, inserting the insertion end 270 of the applicator 210 into the vagina 92 through the vaginal opening 91, and pushing the plunger 240 to eject the pledget 150 from the applicator 210. In some aspects, the method further comprises adjusting the pressure exerted by the device 210 by pulling on the withdrawal member while the applicator 210 is disposed in the vagina 92. In some aspects, the method further comprises removing the urinary incontinence device 110 from the vagina 92 by pulling on the withdrawal member 56.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. A disposable urinary incontinence device comprising a liquid-stable resilient member, and a cover sheet that envelops the liquid-stable resilient member to form an elongated member having a tubular profile;

wherein the elongated member has a first end, a second end, a first fold region disposed between the first end and the second end, a second fold region disposed between the first end and the first fold region, a third fold region disposed between the second end and the first fold region, a first portion located between the first end and the second fold region, a second portion located between the second end and the third fold region, a third portion located between the first fold region and the second fold region, and a fourth portion located between the first fold region and the third fold region;

wherein the elongated member is in a folded condition such that the first portion is substantially aligned adjacent to the second portion, the first portion is substantially aligned adjacent to the third portion, the second portion is substantially aligned adjacent to the fourth portion, and the first portion and the second portion are disposed between and adjacent to the third portion and the fourth portion to form a disposable urinary incontinence device having a W-shaped profile.

2. The disposable urinary incontinence device of claim 1, wherein the liquid-stable resilient member is non-absorbent, as measured by the Spinning Retention Capacity Test.

3. The disposable urinary incontinence device of claim 1, wherein the liquid-stable resilient member has a resilient compression from 60% to 90% and a resilient expansion from 60% to 100%, as measured by the Resiliency Test.

4. The disposable urinary incontinence device of claim 1, wherein the liquid-stable resilient member is a surge material comprising a plurality of thermoplastic fibers heat bonded to one another to form a lofty nonwoven web having a basis weight of at least 20 grams per square meter, a void volume of between 80 and about 120 centimeters per gram of web while under a pressure of 689 dynes per square centimeter, a permeability of about 8,000 to about 15,000 darcy, a porosity of at least 95 percent, a surface area per void of 10 to 25 square centimeters per cubic centimeter and a compression resilience of at least about 60 percent.

5. The disposable urinary incontinence device of claim 4, wherein the thermoplastic fibers comprise at least one of polyolefins, polyesters, polyamides, orlon, acetates or polyvinyl alcohol.

6. The disposable urinary incontinence device of claim 1, further comprising an additional non-absorbent layer, wherein the additional non-absorbent layer is adjacent a planar surface of the liquid-stable resilient member.

7. The disposable urinary incontinence device of claim 1, wherein the tubular profile is with respect to a longitudinal axis.

8. The disposable urinary incontinence device of claim 1, wherein the elongated member comprises an end seal at the first end and at the second end, each of which is substantially free of the resilient member.

9. The disposable urinary incontinence device of claim 1, further comprising a fold guide in the form of an embossment disposed on the cover sheet.

10. The disposable urinary incontinence device of claim 1, wherein the cover sheet comprises at least one of polyethylene or polypropylene.

11. The disposable urinary incontinence device of claim 1, wherein the cover sheet is hydrophobic.

12. The disposable urinary incontinence device of claim 1, further comprising a first aperture adjacent the first end of the elongated member and a second aperture adjacent the second end of the elongated member, wherein the first aperture and the second aperture are substantially aligned in the W-shaped profile-folded elongated member.

13. The disposable urinary incontinence device of claim 12, wherein the first aperture is located from 2 mm to 20 mm from the first end and the second aperture is located from 2 to 20 mm from the second end.

14. The disposable urinary incontinence device of claim 12, further comprising a withdrawal member, wherein the withdrawal member is present in both the first aperture and the second aperture.

15. The disposable urinary incontinence device of claim 14, wherein the withdrawal member is in the form of a string.

16. The disposable urinary incontinence device of claim 1, having a transverse device compression from 100 $g_f$ to 900 $g_f$ as measured by the Transverse Device Compression Test.

17. The disposable urinary incontinence device of claim 1, wherein the disposable urinary incontinence device having a W-shaped profile has been compressed to form a pledget having an insertion end and a trailing end.

18. The disposable urinary incontinence device of claim 17, wherein the pledget has substantially equivalent wet and dry expansion characteristics.

19. The disposable urinary incontinence device of claim 17, further comprising an applicator having an insertion end and a trailing end, wherein the pledget is disposed within the applicator such that the insertion end of the pledget is adjacent the insertion end of the applicator.

20. The disposable urinary incontinence device of claim 1, wherein the applicator comprises: a tapered barrel having an insertion end, a trailing end and an elliptical cross-section profile; a gripping portion having an insertion end, a trailing end and a finger contour; and a hollow plunger having an insertion end, a trailing end, a head flange, a rear flange, and a shaft portion; wherein the insertion end of the gripping portion is connected to the trailing end of the barrel; and wherein the head flange and at least part of the shaft portion are disposed within the gripping portion.

* * * * *